United States Patent
Seul et al.

(10) Patent No.: US 7,211,183 B2
(45) Date of Patent: *May 1, 2007

(54) ANALYSIS AND FRACTIONATION OF PARTICLES NEAR SURFACES

(75) Inventors: Michael Seul, Fanwood, NJ (US); Sukanta Banerjee, North Brunswick, NJ (US); Kairali Podual, North Brunswick, NJ (US)

(73) Assignee: BioArray Solutions Ltd., Warren, NJ (US)

( * ) Notice: Subject to any disclaimer, the term of this patent is extended or adjusted under 35 U.S.C. 154(b) by 755 days.

This patent is subject to a terminal disclaimer.

(21) Appl. No.: 10/658,070

(22) Filed: Sep. 9, 2003

(65) Prior Publication Data

US 2004/0129568 A1    Jul. 8, 2004

Related U.S. Application Data

(63) Continuation-in-part of application No. 09/813,571, filed on Mar. 21, 2001, now Pat. No. 6,706,163.

(51) Int. Cl.
  *B01D 57/02* (2006.01)
(52) U.S. Cl. .................. 204/549; 204/547; 204/643; 204/645; 204/450; 204/600
(58) Field of Classification Search ............... 204/547, 204/549, 643, 645, 450, 600
See application file for complete search history.

(56) References Cited

U.S. PATENT DOCUMENTS

| | | |
|---|---|---|
| 4,046,667 A | 9/1977 | Goetz |
| 4,102,990 A | 7/1978 | Uzgiris |
| 4,497,208 A | 2/1985 | Oja et al. |
| 4,602,989 A | 7/1986 | Culkin |
| 4,679,439 A | 7/1987 | Culkin |
| 4,702,598 A | 10/1987 | Bohmer |
| 4,911,806 A | 3/1990 | Hofmann |
| 5,015,452 A | 5/1991 | Matijevic |
| 5,308,586 A | 5/1994 | Fritsche et al. |
| 5,846,708 A | 12/1998 | Hollis et al. |

(Continued)

FOREIGN PATENT DOCUMENTS

DE    4035714 A1    5/1992

(Continued)

OTHER PUBLICATIONS

Heiger, "Electro-osmotic flow (EOF)", (1997) High Performance Capillary Electrophoresis—An Introduction, Hewlett Packard Company, 3rd Edition, 15-22.

*Primary Examiner*—Nam Nguyen
*Assistant Examiner*—Surekha Vathyam
(74) *Attorney, Agent, or Firm*—Eric Mirabel

(57) ABSTRACT

A method and apparatus for fractionation of a mixture of particles and for particle analysis are provided, in which LEAPS ("Light-controlled Electrokinetic Assembly of Particles near Surfaces") is used to fractionate and analyze a plurality of particles suspended in an interface between an electrode and an electrolyte solution. A mixture of particles are fractionated according to their relaxation frequencies, which in turn reflect differences in size or surface composition of the particles. Particles may also be analyzed to determine their physical and chemical properties based on particle relaxation frequency and maximal velocity.

26 Claims, 15 Drawing Sheets

U.S. PATENT DOCUMENTS

| | | |
|---|---|---|
| 5,888,370 A | 3/1999 | Becker et al. |
| 6,120,666 A | 9/2000 | Jacobson et al. |
| 6,122,599 A | 9/2000 | Mehta |
| 6,132,685 A | 10/2000 | Kercso et al. |
| 6,136,171 A | 10/2000 | Frazier et al. |
| 6,193,866 B1 | 2/2001 | Bader et al. |
| 6,251,691 B1 | 6/2001 | Seul |
| 6,254,754 B1 | 7/2001 | Ross et al. |
| 6,294,063 B1 | 9/2001 | Becker et al. |
| 6,358,387 B1 | 3/2002 | Kopf-Sill et al. |
| 6,387,707 B1 | 5/2002 | Seul et al. |
| 6,426,615 B1 | 7/2002 | Mehta |
| 6,515,649 B1 | 2/2003 | Albert et al. |
| 6,706,163 B2 * | 3/2004 | Seul et al. .......... 204/549 |
| 2001/0019133 A1 | 9/2001 | Konuma et al. |

FOREIGN PATENT DOCUMENTS

WO    WO 97/40385    * 10/1997

* cited by examiner

Simulated bead velocity as a function of position for a bead of diameter 3.2 μm, surface potential 200 mV and ionic strength 0.1 mM, voltage 5 V (peak-to-peak), gap width 150 μm.

ANALYSIS AND FRACTIONATION OF PARTICLES NEAR SURFACES

RELATED APPLICATIONS

This application is a continuation-in-part of U.S. application Ser. No. 09/813,571, filed Mar. 21, 2001 (now U.S. Pat. No. 6,706,163).

GOVERNMENT SPONSORSHIP

This invention was made with government support under contract No. DaaH01-98-C-R053 awarded by the Defense Advanced Research Projects Agency. The government may have certain rights in the invention.

FIELD OF THE INVENTION

The present invention generally relates to the fields of analytical chemistry and materials characterization. Specially, the present invention relates to fractionation of heterogeneous mixtures of particles on the basis of characteristic frequency dependence of particle polarization and also to analysis of electrochemical properties of particles.

BACKGROUND OF THE INVENTION

I.1 Methods of Fractionation and Sorting

Among analytical separation techniques, methods of flow cytometry have been used in sorting of particles (including cells) within a given heterogeneous population. These methods, however, require a dedicated instrument capable of selecting and physically separating from the population those particles which satisfy a given selection criterion. For example, the objective of cell sorting by flow cytometry usually is the selection of those cells within a population displaying a characteristic fluorescence signal.

I.2 Methods of Particle Analysis

Particle analysis represents a standard procedure of the analytical chemical repertoire that is used to determine physico-chemical and compositional properties [Hunter, "Introduction to Modern Colloid Science", Oxford University Press, Oxford, UK, 1993]. The extensive repertoire of techniques reflects the ubiquitous use of particles of a wide range of sizes, shapes, composition and chemical reactivity in many scientific and industrial applications ranging from medical diagnostics to cosmetics. Characterization of particles is useful in guiding and optimizing production as well as chemical modification particularly of surface properties that determine the stability of particle suspensions and the interaction of particles with molecules in the surrounding medium.

Techniques of the standard repertoire may be grouped as follows: first, sedimentation and centrifugation methods, electroacoustics, light scattering, hydrodynamic methods and dielectric spectroscopy; second, electrical pulse counting, flow cytometry and electrophoretic zeta potential measurements; third, specialized methods including dielectrophoresis (DEP), including its combination with field-flow fractionation methodology.

Methods in the first group apply to bulk suspensions and therefore deliver an average of the measured quantities for a large number of particles. While desirable in situations in which large industrial batches are to be characterized, bulk measurements generally do not lend themselves to miniaturization and are not well suited to the characterization of small numbers of particles, particularly when particle-to-particle variations are of interest or when multiple particle parameters are to be determined simultaneously.

Methods in the second group use a "single-file" serial format of measurement. While these methods determine the properties of individual particles, their implementation, in order to attain sufficiently high processing rates, requires high flow rates of a carrier gas or fluid and high-speed data recording and read-out electronics, generally rendering the equipment complex and expensive. This is so especially when multiple parameters are to be determined for each particle. For example, multi-color detection in flow cytometers can require the use of multiple lasers and multiple photomultiplier tubes. The determination of the zeta potential along with particle size in state-of-the-art equipment requires the measurement of electrophoretic mobility of particles traveling along a narrow capillary in response to a DC voltage applied along the channel as well as the application of light scattering with associated light source and read-out, as in the ZetaSizer (Malvern Instruments, Southborough, Mass.). Miniaturization, as in the case of flow cytometry [Fu, AX, Spence, C., Scherer, A., Arnold, F. H. and Quake, S. R. A Microfabricated Fluorescent-Activated Cell Sorter, Nature Biotechnology, Vol. 17, November 1999, 1109–1111], retains the serial mode of processing and thus encounters the constraint of limited throughput.

Methods in the third group include various dielectrophoretic techniques to characterize, classify and fractionate low conductivity particle suspensions [Becker, F. F., Gascoyne, P. R. C., Huang, Y. and Wang, X-B, Method and Apparatus for Fractionation Using Generalized Dielectrophoresis and Field Flow Fractionation, U.S. Pat. No. 5,888,370, Mar. 30, 1999; Rousselet, J., Markx, G. H. and Pethig, R., Separation of Erythrocytes and Latex Beads by Dielectrophoretic Levitation and Hyperlayer Field-Flow Fractionation, Colloids and Surfaces A: Physicochemical and Engineering Aspects, 140 (1998) 209–216; Pethig, R., Markx, G. H., Apparatus for Separating by Dielectrophoresis, U.S. Pat. No. 5,814,200, Sep. 29, 1998; Pohl, H. A., Continuous Dielectrophoretic Cell Classification Method, U.S. Pat. No. 4,326,934, Apr. 27, 1982; Parton, A., Huang, Y., Wang, X-B., Pethig, R., MacGregor, A. R., and Pollard-Knight, D. V., Methods of Analysis/Separation, U.S. Pat. No. 5,653,859, Aug. 5, 1997; Crane, S., Dielectrophoretic Cell Stream Sorter, U.S. Pat. No. 5,489,506, Feb. 6, 1996; Benecke, W., Wagner, B., Hagedorn, R., Fuhr, G., Muller, T., Method of Continuously Separating Mixtures of Microscopic Dielectric Particles and Apparatus for carrying through this method, U.S. Pat. No. 5,454,472, Oct. 3, 1995]. All publications which are cited throughout the application are hereby incorporated by reference in their entirety.

Coupled with a suitable imaging system, techniques within this group can provide single particle information. The particle classification is achieved by exposing the particle mixture to a non-uniform AC electric field which is generated by applying an AC voltage to multiple sets of planar patterned microelectrodes. Such a scheme in general requires a complex electrode signaling/addressing scheme. Also, a continuous mode of operation requires, in the simplest case, coupling to an external flow or the use of field flow fractionation. Simple dielectrophoretic setups do not generally allow for quantitative evaluation for the surface potential or surface conductivity of particles. While these quantities maybe determined from electrorotation spectra of single particles, this approach requires a complex and time-consuming set-up to confine a single particle at the origin of a rotating electric field whose frequency is scanned while recording the rotational motion of the confined particle. Aside from the complexity of the equipment required to implement the requisite experimental configuration, the low throughput of the method presents a serious disadvantage when averages of multiple particles are desired.

SUMMARY OF THE INVENTION

The present invention provides a method and apparatus for the fractionation of a mixture of particles and for the analysis of particles, based in part on the technology designated "LEAPS", described in PCT International Application No. WO 97/40385 To Seul. The present invention uses LEAPS (referring to "Light-Controlled Electrokinetic Assembly of Particles near Surfaces") to fractionate a heterogeneous mixture of particles on the basis of, e.g.: morphological properties including size and shape; surface composition relating to certain electrochemical properties, including surface potential and surface conductivity; and specific and non-specific adhesion to exposed surfaces provided within the apparatus. As used herein, the term "fractionation" refers to separation or sorting of particles, including separation of multi-component particle mixtures into their constituent subpopulations. Particles may be separated on the basis of the characteristic frequency dependence of the particle polarization, said dependence reflecting physical or chemical properties of the particles.

The present invention also provides for the use of LEAPS to determine various physical or chemical properties of particles, including morphological properties, surface electrochemical properties and surface chemical properties such as the particles adhesiveness for given surfaces of the apparatus or for other particles.

The present invention provides a method and apparatus for fractionation of particle mixtures on the basis of the respective characteristic relaxation frequencies of the constituent particles or particle populations. In certain embodiments of such method, a plurality of particles are suspended at an interface between an electrolyte solution and a light-sensitive electrode. The particles comprise at least two types, each type having a distinguishable relaxation frequency. An electric field, having a frequency that is less than or equal to the relaxation frequency of at least one of said particle types but greater than the relaxation frequencies of other particle types, is generated at the interface by application of an AC voltage. In addition, the interface is illuminated with a predetermined light pattern. The illumination in combination with the electric field produces fractionation of the particles having relaxation frequencies greater than or equal to the frequency of the electric field from other particles, e.g., by assembly of particles having a relaxation frequency greater than the frequency of the applied electric field resulting in formation of a planar array of substantially one layer of particles in an area on the electrode designated by the pattern of illumination. In certain embodiments, the illumination affects the electrolyte-electrode interfacial impedance.

In certain preferred embodiments, the electrode comprises a silicon electrode which is coated with a dielectric layer. In certain preferred embodiments, an additional electrode is provided such that the light-sensitive electrode and the additional electrode are substantially planar and parallel to one another and separated by a gap (e.g., in a sandwich configuration), with the electrolyte solution containing the particles being located in the gap.

In certain other embodiments of the present invention, patterned electrode is used instead of or in combination with the illumination to fractionate a mixture of particles. In one such example, a first electrode positioned in the first plane and a second electrode positioned in the second plane different from the first plane is provided with a gap between the electrodes, an arrangement herein referred to as a sandwich configuration. A mixture of particles is suspended in an electrolyte solution and located in the gap. The second electrode comprises a planar electrode having a surface and an interior, either of which may be patterned to modify the spatial distribution of the interfacial (interface between the electrolyte solution and the second electrode) electric field. When an electric field is generated between the first and the second electrode by applying an AC voltage between the two, the electric field in combination with the patterning of the electrode produces fractionation of the particles according to relaxation frequency; for example, particles having a relaxation frequency greater than the frequency of the applied electric field move toward designated regions of the second electrode surface as provided by illumination or patterning and therein form a planar array of substantially one layer. In preferred embodiments, the second electrode may be patterned by spatially modulated oxide growth, surface chemical patterning or surface profiling (which is described in U.S. Ser. No. 09/171,550, filed Oct. 26, 1998, now U.S. Pat. No. 6,251,691 issued Jun. 26, 2001); preferably, the patterning affects the impedance of the electrolyte solution and second electrode interface. In preferred embodiments, the second electrode comprises a silicon electrode which is coated with a dielectric layer.

In certain embodiments, the difference in relaxation frequency of particles within a heterogeneous mixture corresponds to a difference in particle size or surface composition, thus permitting fractionation of the mixture into homogeneous subpopulations of particles according to size or surface composition, respectively. The process of fractionation may also be monitored using a video detector or camera.

Accordingly, the present invention provides a method and apparatus for fractionation of particle mixtures based on the characteristic relaxation frequencies of said mixture's constituent particles or particle subpopulations. The present invention provides for the determination of the frequency dependence of the electrohydrodynamic forces that govern particle transport into designated low-impedance areas of the electrode and mediate formation of particle arrays in those designated areas. As described herein, a particle relaxation frequency, $\omega_R$, is a property that is associated with the particle-solution interface and may be determined from the condition that array assembly requires that the frequency $\omega < \omega_R$: particles not meeting this criterion will be excluded from low-impendance areas.

The present invention also provides for a method and apparatus for the analysis of particles in order to determine various physical or chemical properties of said particles, including size, morphology, surface potential and surface conductivity. For example, the relaxation frequency and/or maximal velocity of transport of the particles are used for particle characterization.

In certain embodiments of the present invention, a plurality of particles suspended in an interface between an electrolyte solution and a light-sensitive or a patterned electrode are provided, as described above in connection with particle fractionation. When an electric field is generated at the interface by the application of an AC voltage, the frequency of the electric field is adjusted to produce formation of a planar array of substantially one layer of particles in an area designated by the pattern of illumination or electrode patterning. From the analysis of particle transport in the course of array assembly, the relaxation frequency and the maximal velocity of transport of the particles may be determined. Alternatively, the particle relaxation frequency also may be determined by analyzing the response of the array configuration to changes in the frequency of the applied electric field.

The present invention also provides for the determination of the frequency-dependent and voltage-dependent maximal velocity, $V_{max}$ attained by particles crossing impedance gradients in the course of array assembly. As described herein, $V_{max}$ may be determined by image analysis and particle tracking. In certain embodiments, the combination of $\omega_R$ and $V_{max}$ provides for the simultaneous determination of the particles' surface ("zeta") potential, $\phi_s$, and surface conductivity, $\sigma$, e.g., based on numerical analysis of phenomenological equations of particle motion described herein.

Once these values are found, they may be used to characterize the particles, e.g., determine the zeta potential of the particles and/or the mobility of ions or molecules within the electrolyte solution in proximity to the particle surface. In preferred embodiments, the relaxation frequency and the maximal velocity are used together in particle characterization. In certain preferred embodiments, the present invention permits the simultaneous determination of multiple particle properties, such as zeta potential and ionic or molecular mobility. In other embodiments, the present invention permits the determination of one particle property of interest independently from the determination of others. For example, in certain embodiments, the ionic or molecular mobility associated with the particle-solution interface may be determined from the relaxation frequency alone.

The term "particles," as used herein include colloidal beads, eukaryotic and procaryotic cells, micelles, vesicles, and emulsion droplets. In preferred embodiments, the particles comprise colloidal beads, or eukaryotic or procaryotic cells.

In contrast to prior art methods of fractionation of particle mixtures such as field flow fractionation, the methods of the present invention provide a parallel format based on the manipulation of a multiplicity of individually imaged particles in a simple sandwich geometry which provides for longitudinal and transverse electrohydrodynamic forces to mediate fractionation on the basis of the frequency-dependent polarization of the particles of interest. Specifically, the methods of the present invention provide for the fractionation of one subpopulation of particles at a time from the remainder.

In contrast to prior art methods of sorting such as fluorescence-activated particle and cell sorting, the methods of the present invention provide for a parallel process accommodating a multiplicity of particles thereby enhancing processing speed. The methods of present invention also are well suited for miniaturization.

In contrast to prior art methods of particle analysis which are applied to bulk particle suspensions and yield ensemble averages of the particle properties of interest, the methods and apparatus of the present invention provide for the miniaturization of the processes of analysis. In contrast to prior art serial methods of analysis of particle mobility, the methods of present invention invoke a collective phenomenon of particle array assembly as the basis for a parallel mode of simultaneous analysis of multiple particle properties accessible either to imaging and image analysis or to light scattering. The methods of the present invention provide for the simultaneous, yet independent determination of morphological parameters including size, orientation and polydispersity, as well as for electrochemical parameters including surface potential and surface conductance.

In contrast to these prior art methods, the implementation of the fractionation methods of the present invention are readily suitable for miniaturization and integration with additional preparative and analytical procedures in an integrated analytical environment.

DETAILED DESCRIPTION OF THE INVENTION

I. Electrostatic Theory of Dielectric Media

Figure 1:
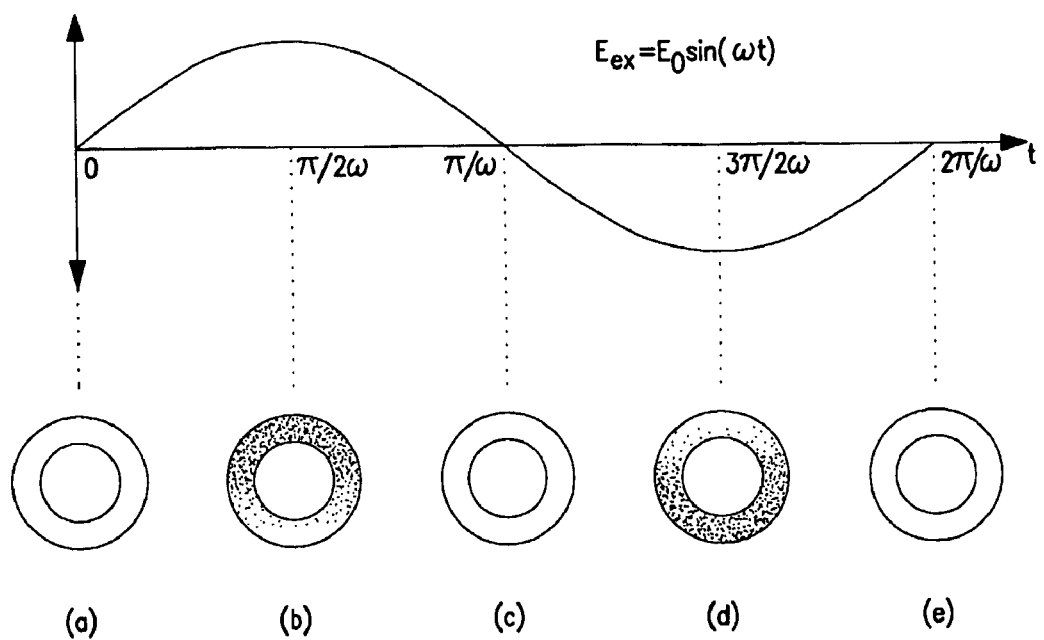
FIG. 1 is an illustration of the response of a polarizable double layer around a spherical particle to a time-varying electric field. The progression of polarization states occurring in a single cycle is shown in panels (a)–(e). The shading indicates the distribution of the predominant type of ion in the diffuse layer.

So that the present invention may be better understood, certain results from the electrostatic theory of dielectric media are herein summarized, making general reference to Landau, Lifshitz & Pitaevskii, "Electrodynamics of Continuous Media", Butterworth-Heinemann, Oxford, UK, 1998.

I.1 Ponderomotive Forces

The free energy of a dielectric medium of dielectric constant $\epsilon_M$ filling a gap of size H between two parallel capacitor plates of area A carrying a charge Q is given by $\Im_0 = -\frac{1}{2} C_0 \phi^2$, where the capacitance, $C_0 = \epsilon_M A/H$, describes the proportionality between applied potential and stored charge, $Q = C_0 \phi$. Under the assumption that the electrostatic potential of the plates remains unchanged, the introduction of a sphere of radius $\alpha \ll H$ and dielectric constant $\epsilon_s$ into the gap changes the free energy in accordance with the following expression:

$$\Im = -\frac{1}{2} C_0 \phi^2 - \frac{1}{2} \varepsilon_M k E_0^2 \quad (1)$$

Here, the factor $k = (\epsilon_s - \epsilon_M)/(\epsilon_s + 2\epsilon_M)$ determines the potential of an uncharged dielectric sphere of radius R and dielectric constant $\epsilon_s$ embedded in a dielectric medium of dielectric constant $\epsilon_M$ and subjected to a homogeneous electric field $E_0$.

$$\phi = -E_0 r \cos\theta \left(1 - \frac{ka^3}{r^3}\right), \quad r > a \quad (2)$$

In accordance with Eq. (1), as long as $\epsilon_M < \epsilon_s$, insertion of the sphere into the dielectric medium in fact lowers the free energy. Consequently, a sphere placed just outside the edges of the plates will be drawn into the space between the plates by a force $F \sim \nabla \Im$. From Eq. (1), with $E_0 = \phi/H$:

$$F = 2\pi\epsilon_M \epsilon_0 k V E^2 \quad (3)$$

This ponderomotive force thus arises from the interaction of the polarization of the sphere with spatial non-uniformities in the electric field. Eq. (3) shows that the force is independent of the sign of the electric field. That is, in a non-uniform electric field, a polarizable particle will move either into or out of a region of higher field, as determined solely by the relative magnitude of the dielectric constants of particle and suspending medium. In general, as discussed herein, the polarization factor k will depend on frequency: $k = k(\omega)$.

I.2 Interfacial Polarization in Electrolyte Solutions

The polarization of a fluid medium, herein referred to as an electrolyte solution, typically manifests itself in the form of gradients in the spatial distribution or orientation of the constituent molecules. Thus, electrolyte solutions are polarized near any interface with a bounding (boundary) surface or interface. When such an interfacial region is subjected to an external electric field of varying frequency, the response of the medium is determined by the processes mediating redistribution or reorientation of the constituent molecules and by characteristic molecular mobilities associated with these processes.

Spatial Distribution of Free Ions: The Double Layer—The response of an electrolyte containing mobile charges to the presence of a charged bounding surface is the formation of a layer of excess charge adjacent to the surface so as to screen the field generated by the charges on that surface. Thus, the polarization of the interface between a charged particle and an electrolyte containing free ions manifests itself in the form of a redistribution of ions so as to form screening shell of excess counterions. This "double layer" is characterized by a surface potential, $\phi_s$, which corresponds to an excess of free charge carriers adjacent to the sphere and by a characteristic screening length, $\kappa^{-1}$, which is directly related to the ionic strength, $\frac{1}{2}\Sigma n_{i0} z_i^2$, of the medium; for a 1:1 electrolyte, $\kappa^{-1} = (\epsilon_M \epsilon_0 k_B T/2z^2 e^2 n_0)^{1/2}$, where $n_0$ is the molar concentration of the electrolyte and z is the charge on each ion. The local excess concentration of ions can affect binding reactions involving molecules anchored to the sphere surface. A uniform electric field induces the redistribution of ions adjacent to and within the "double layer", leading to a phenomenon sometimes referred to as "concentration polarization" (FIG. 1). The redistribution of the molecules forming the screening layer is determined by translational molecular mobilities.

Preferred Orientation of Dipolar Molecules—The response of an electrolyte containing dipolar molecules to the presence of a charged bounding surface is the formation of a layer in which those molecules assume a preferred orientation. As with the previous case, the interfacial region of preferred molecular orientation is characterized by a surface excess polarization and a characteristic decay length which is readily determined from a statistical theory. The local excess orientation can affect binding reactions involving molecules anchored to the sphere surface. The redistribution of the molecules forming the screening layer is determined by orientational molecular mobilities. In any given electrolyte, excess concentration and orientation (as well as higher moments of the molecular charge distribution) may contribute to the formation of a screening layer.

I.3 Frequency Dependence of Field-Induced Polarization

An externally applied electric field alters the interfacial polarization of electrolytes by inducing the redistribution or reorientation of the constituent molecules. Thus, an applied AC electric field induces a time-dependent interfacial polarization. As with the recharging of a parallel plate capacitor, the time-dependent interfacial polarization corresponds to a transient charging current, $j \sim \partial_t P$. When the time-dependent interfacial polarization is mediated by the spatial redistribution of free ions, the charging current, $j$, will be composed of a longitudinal and a transverse component, respectively reflecting the redistribution of ions within the double layer and the exchange of charge between the double layer and the surrounding medium. Set forth below are certain results for this case; it is noted that corresponding results also may be cited for the time-dependent reorientation of dipolar molecules.

The longitudinal component reflects the redistribution of primarily of counterions within the double layer in response to the applied field on a characteristic time scale $\tau_\parallel \sim (\alpha+1/\kappa)^2/D \sim 1/\omega_R$, where $\alpha$, $1/\kappa$ and $D$ respectively denote: the particle radius, the Debye screening length and a characteristic diffusivity of the majority carrier. The characteristic time scale, $\tau = \tau_\parallel$, is determined primarily by the counterion mobility, $u \sim ze/f$, where n and f respectively denote the local counterion concentration and drag coefficient. Ionic mobilities in the vicinity of the particle surface will reflect the details of the local chemical environment and generally will differ significantly from the corresponding value in the bulk medium. By invoking the Einstein relation $1/f = D/k_B T$, the relaxation frequency, $\omega_R$, may be expressed in terms of the counterion mobility, u:

$$\omega_R \cong \frac{D\kappa^2}{(1+a\kappa)^2} = \frac{\kappa^2}{(1+a\kappa)^2}(k_B T/e)u \quad (4)$$

The longitudinal counterion current is balanced by a transverse current reflecting the radial transport of co- and counterions across the double layer on a time scale $\tau_\perp \sim 1/\kappa^2 D \sim 1/\omega_\perp$. If electroneutrality is to be strictly maintained in the electrolyte adjacent to the double layer, then the exchange of counterions between double layer and surrounding electrolyte via radial transport must be accompanied by the radial transport of an equal number of coions. The result is a change in the local ionic strength in the electrolyte adjacent to the double layer. That is, gradients in electrolyte concentration appear on the scale of the particle diameter, and these decay away on a characteristic time scale $\tau \sim 1/\omega_R$. As the frequency increases, the redistribution of ions within the double layer eventually will no longer suffice to attain the fully polarized state; relaxation occurs when $\omega_R \tau \simeq 1$. For a typical particle radius of 1 μm, and a typical value $\omega_\perp \simeq 10^5/s$, the relaxation frequency, $\omega \sim \omega_\perp/(1+\kappa\alpha)^2$ is approximately 1 kHz.

Phenomenological Theory for Polarization Factor $k(\omega)$—
Phenomenological models have been developed to relate the field-induced, frequency-dependent polarization, $k = k(\omega)$ to the particle's surface potential, $\phi_s$, and to the surface conductivity, $\sigma$. The former, for given bulk ionic strength, determines the total charge density within the double layer; the latter determines the rate at which the double layer is able to readjust in response to a time-varying applied field. Specifically, a linearized theory, valid for small surface potentials, is available to treat the contribution of transverse ionic fluxes to the transient ionic charging currents and the charge balance within the double layer to produce an expression for the frequency dependence of $k = k(\omega)$ [Dukhin and Shilov, "Dielectric Phenomena and the Double Layer in Disperse Systems and Polyelectrolytes", Keter Publishing, Jerusalem, 1974]. A recent formulation of the linearized theory of the electrokinetic transport phenomena underlying concentration polarization, developed for the analysis of the low-frequency dielectric response of colloidal suspensions, yields a useful analytical form for the frequency dependence of $k(\omega)$ [Minor et al, J. Colloid & Interface Science 206, 397–406 (1998)].

Assuming low values of the external field, the potential and the ion distribution(s) are linearized around the equilibrium condition existing in the absence of an external field. For the region within the suspending medium far from the double layer, ion balances (for the i-th species) obey the Nernst-Planck equation:

$$\frac{f_i^\infty}{k_B T} \frac{\partial \delta n_i^f}{\partial t} = \nabla^2 \left[ n_i^\infty \frac{z_i e}{k_B T} \delta\phi^f + \delta n_i^f \right] \quad (5)$$

Here, the terms preceded by 'δ' denote the respective first order deviations from the corresponding equilibrium values, and f is an effective friction factor which governs the ion mobility. Solving Eq. (5) along with the linearized Poisson equation, expressions for $\delta n_i^f$; f and $\delta\phi^f$ are found as follows:

$$\delta n_i^f = \frac{d_{i,n} a^3 E_0}{r^2}(1+\lambda)\exp(-\lambda r)\cos(\theta)\exp(i\omega t) \quad (6)$$

$$\delta\phi^f = -E_0 r\left(1 - \frac{ka^3}{r^3}\right)\cos(\theta)\exp(i\omega t) - \frac{k_B T}{ef^\infty}\frac{\delta n_i^f}{n_i^\infty}$$

Here, $\lambda a = (1+i)(\omega\tau)^2$; the time scale, $\tau$, is set by the characteristic diffusion time for transport around the perimeter of the particle: $\tau \cong a^2/D = f^\infty a^2/2k_e T$ The polarization parameter, k, determines the increase in the effective dielectric constant of the medium due to the presence of particles and associated double layers. To express $k = k(\omega)$ in terms of system properties of interest, boundary conditions are applied to Eq. (6) in the form of a flux balance: tangential ion fluxes within the double layer are balanced by radial ion fluxes into and out of the double layer so as to ensure that electroneutrality is maintained in the external solution at all times. Restricting attention to an electrolyte containing only a single coion (superscript "1") and a single counterion species (superscript "2") and ignoring the coion flux within the double layer as negligible compared to the counterion flux, the flux balance at the outer edge ($r = \alpha^+$) of the double layer is expressed in the form:

$$\frac{\partial}{\partial r}\left[n_2^\infty \frac{z_2 e}{k_B T}\delta\psi^f + \delta n_2^f\right]\bigg|_{r=a^+} + Du_2 a \nabla_t^2 \left[n_2^\infty \frac{z_2 e}{k_B T}\delta\psi^f + \delta n_2^f\right]\bigg|_{r=a^+} = 0 \quad (7)$$

where $\nabla_t$ denotes a tangential gradient operator. Radial and tangential counterion fluxes are related by the constant, $Du_2$, which represents the dimensionless ratio of (the counterion-mediated) surface conductivity to (the counterion-mediated) bulk conductivity, $Du_2 = \sigma/a\sigma_\infty$, $\alpha$ denoting the particle diameter. $Du_2$ may be expressed in terms of the surface potential, $\phi_s$, and a dimensionless counterion mobility, $m_2$, as follows:

$$Du_2 = \left(\frac{1+|z_1/z_2|}{2}\right)^2 \frac{2}{\kappa a}(1+3m_2/z_2^2)\left[\exp\left(\frac{-z_2 e\phi_s}{2k_B T}\right)-1\right], \quad (8)$$

where $m_2 = \dfrac{2\varepsilon_1 kT f_2^\infty}{3\eta e^2}$

Application of the boundary conditions yields the following expression for the polarization parameter, $k(\omega)$:

$$Kw = -\frac{1}{2} + \frac{3}{2}\frac{Du_2(1+h)}{Du_2[2-\gamma(1-h)]},$$

where $$\gamma \equiv 1 - \frac{1+\lambda a}{1+\lambda a+\frac{1}{2}(\lambda a)^2} = \frac{\omega\tau\sqrt{\omega\tau}+i\omega\tau}{(1+\sqrt{\omega\tau})(1+\omega\tau)}$$

and $$h \equiv \frac{z_2/f_2^\infty + z_1/f_1^\infty}{z_2/f_2^\infty - z_1/f_1^\infty} = \frac{\overline{u}_2^\infty + \overline{u}_1^\infty}{\overline{u}_2^\infty - \overline{u}_1^\infty}$$

Figure 2:
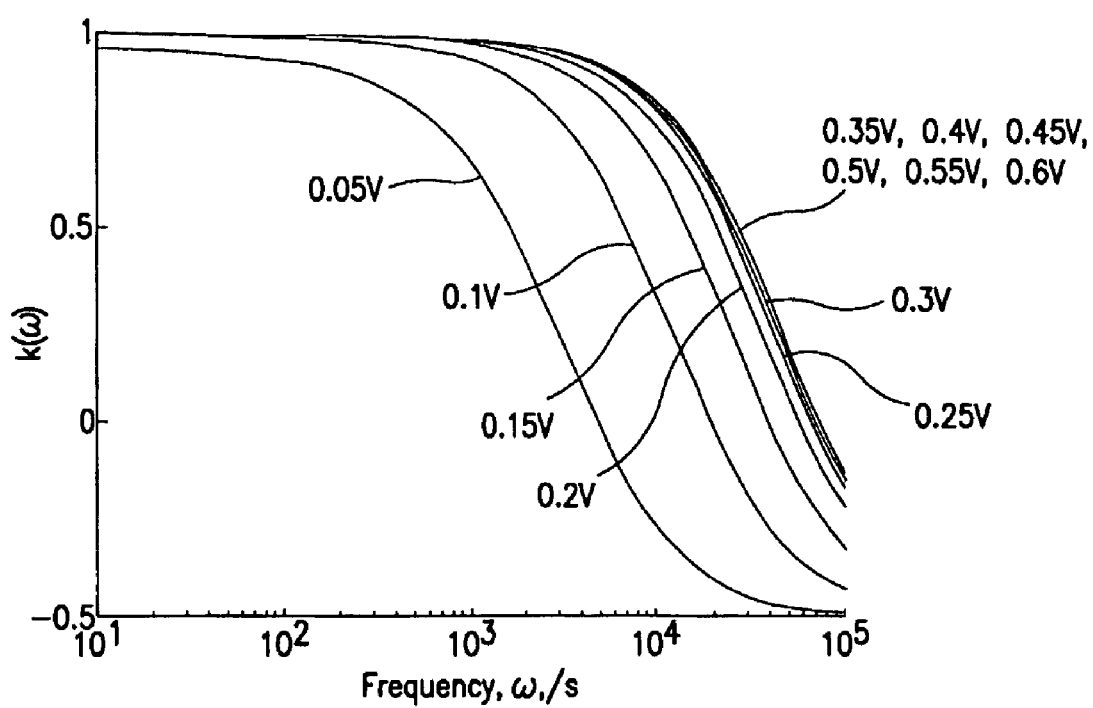
FIG. 2 is an illustration of the variation of the polarization factor of a particle with frequency, as evaluated numerically on the basis of the theoretical model described herein and assuming the indicated values of the particle surface potential, a particle diameter of 2.8 µm and a solution of ionic strength 0.1 mM.
Figure 3A:
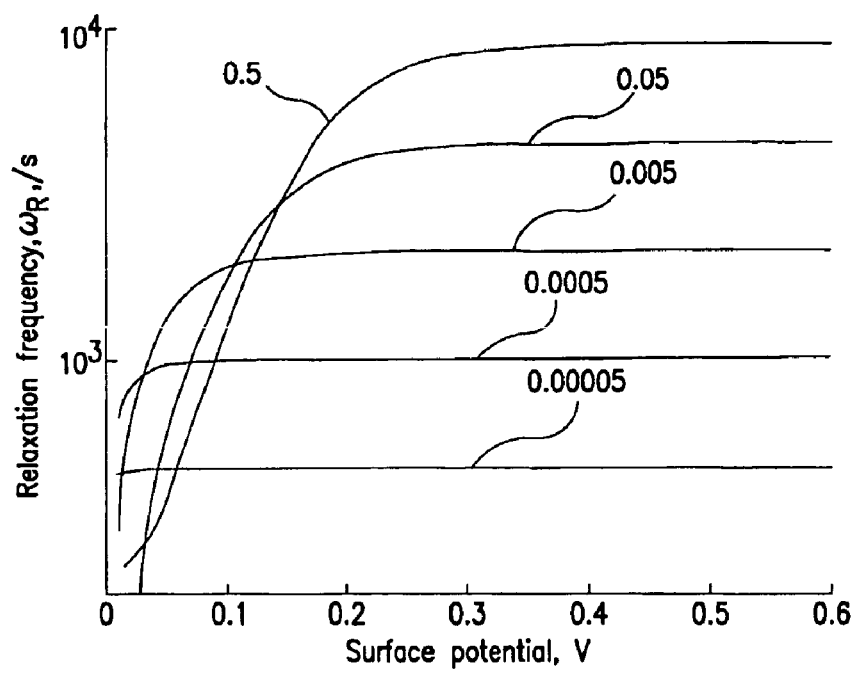
FIG. 3(A) is an illustration of the dependence of the relaxation frequency on surface potential, as evaluated numerically on the basis of the theoretical model described herein for a 2.8 µm particle suspended in a solution of ionic strength 0.1 mM. The legend refers to the ratio of counterion mobility in the double layer to the bulk ion mobility. (B) is a plot of the relation between surface potential and mobility for the specific relaxation frequency of 1000 Hz.
Figure 3B:
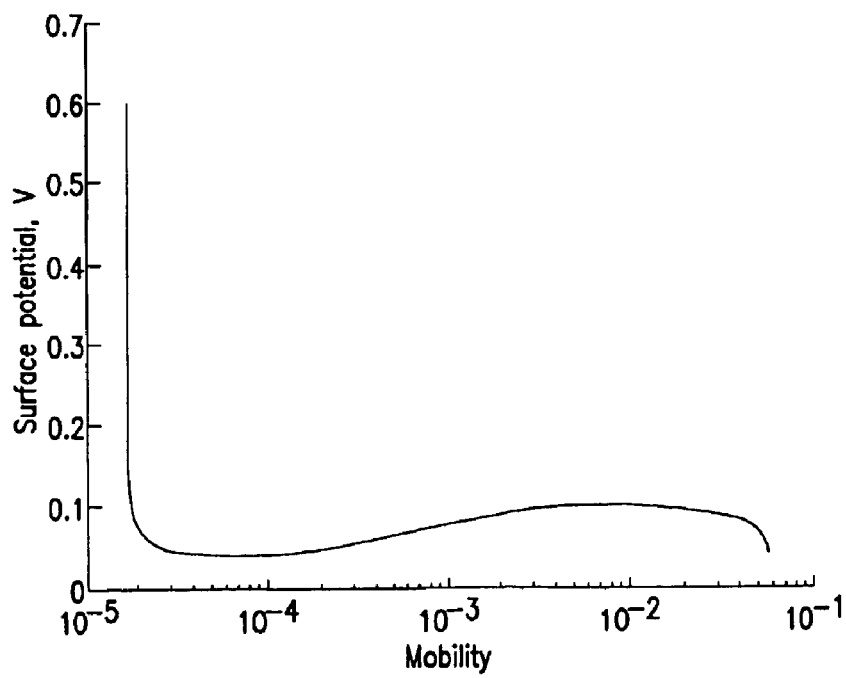

FIG. 2 shows representative plots of $k(\omega)$ for different values of surface potential and for a given ratio of surface ion mobility, u, and bulk ion mobility, $u_\infty$. The point of inflection in each of these plots identifies a peak in the dispersion, which in turn identifies the corresponding frequency as the relaxation frequency, $\omega_R$. The plots in FIG. 3 show that for given value of $u/u_\infty$, $\omega_R$ generally will exhibit a dependence on surface potential. That is, $\omega_R$ may be understood as a function of the ionic conductivity, $\sigma \sim eun \sim ze^2n/f$, a quantity which in turn depends on both ionic mobility as well as local ion density, the latter being controlled by the surface potential.

However, FIG. 3 also shows that, for sufficiently large values of the surface potential, $\phi_s$, the dependence of $\omega_R$ on surface potential vanishes, yielding instead a linear relationship, $\omega_R \sim u/u_\infty$, in accordance with the scaling relation, Eq. 4. This relation, which formed the basis for the analysis of the data in FIG. 10, thus provides the basis for a direct experimental determination of ionic or molecular mobility from a determination of the relaxation frequency.

II. Electrokinetic Particle Transport and Particle Array Assembly

Light-controlled Electrokinetic Assembly of Particles near Surfaces (LEAPS), as disclosed in WO97/40385, enables the formation of planar arrays of particles (including on-cue formation) in designated areas of a substrate under real-time optical control. LEAPS combines the use of electric fields, interfacial patterning and/or light to introduce spatial and temporal modulations of the impedance of an Electrolyte-Insulator-Semiconductor (EIS) interface. LEAPS invokes electrohydrodynamic forces which arise in accordance with the lateral impedance gradients to control the coupled transport of fluid and suspended particles as well as the array assembly process.

The present invention describes the role of polarization-induced forces that contribute to particle transport and array assembly under conditions characteristic of LEAPS. These models guide the selection of conditions for the fractionation of particle mixtures in response to combinations of time-varying electric fields. These models also provide methods for the analysis of coupled fluid-particle transport in order to determine characteristic particle properties of interest.

III. Fluid Flow, Particle Collection and Array Assembly

Figure 4:
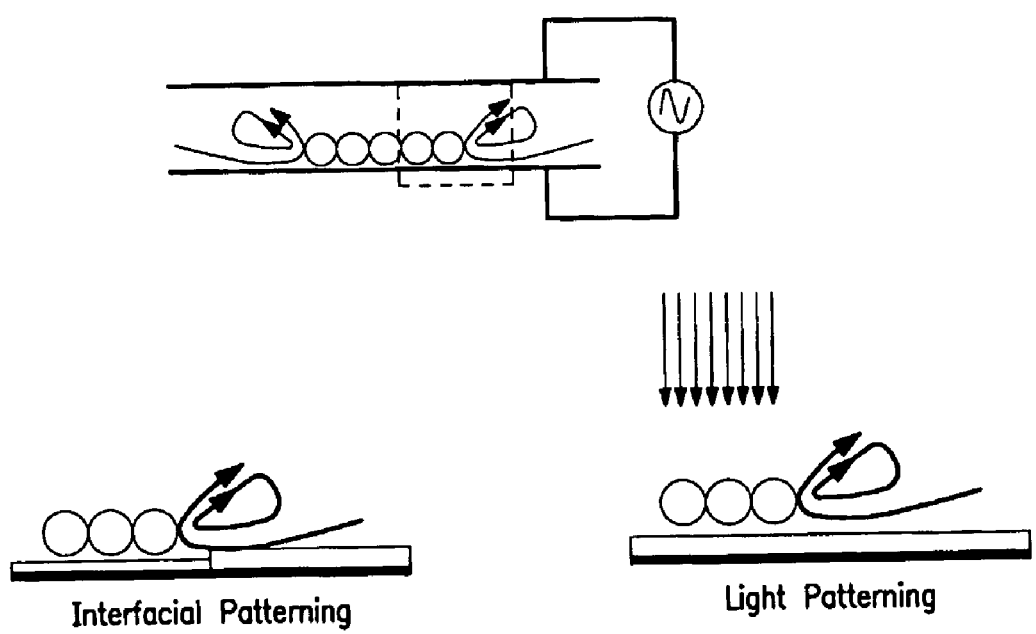
FIG. 4 is an illustration of flow fields characteristic of a sandwich geometry compatible with LEAPS.

Light-controlled Electrokinetic Assembly of Particles near Surfaces (LEAPS) is described in PCT International Application No. PCT/US97/08159 (published as WO 97/40385) and U.S. Ser. No. 09/171,550, filed Oct. 26, 1998 (issued as U.S. Pat. No. 6,251,691 on Jun. 26, 2001) which are incorporated by reference in their entirety. Also incorporated herein by reference in their entirety are U.S. Ser. No. 09/397,793, filed Sep. 17, 1999 (published in WO 01/20593) (describing system and method for programmable illumination pattern generation), as well as U.S. Ser. No. 09/320,274, filed May 28, 1999, and PCT International Application No. PCT/US00/14957 (published as WO 00/73777) (relating to array cytometry). LEAPS involves the interplay between several electrokinetic forces to induce fluid flow, particle transport and array assembly. For example, in a sandwich geometry, an AC electric field applied across a fluid gap generates rectified electroosmotic flow in the vicinity of lateral gradients of the Electrolyte-Insulator-Semiconductor (EIS) impedance that are set up by interfacial patterning or spatially varying illumination (see FIG. 4). Generally, these flows are observed under the condition $\omega \leq \omega_{195}$, the latter characteristic frequency being determined by molecular processes governing the response of the polarization of the EIS interface. Under the action of these flow fields, particles are "collected" over macroscopic distances and are swept from regions of higher toward regions of lower interfacial impedance by viscous drag.

Polarizable particles, while being swept along by the electrokinetic flows, simultaneously respond to the applied electric field; specifically, if particles are charged, the applied field induces local charging currents which in turn create a substantial concentration polarization in accordance with the mechanism previously discussed herein. This field-induced polarization determines the effective dielectric constant of polarizable particles and so dominates the ponderomotive forces exerted on such particles in regions of rapid spatial variations in electric fields such as those produced near steps or other steep gradients in interfacial impedance.

Accordingly, particles approaching a step in EIS impedance come under the influence of the gradient $\nabla(E \cdot E)$ and accelerate across the step into the low impedance region where they are slowed, e.g., by the drag force exerted by the fluid. The particles enter into regions of low impedance and form arrays when $\omega \leq \omega_R$ ("aggregation"); in contrast, when $\omega > \omega_R$, particles accumulate on the high impedance side in the vicinity of the boundary. Illumination also can induce gradients in impedance and, provided that $\omega \leq \omega_R$, array formation in illuminated areas of the electrode.

In certain embodiments of the present invention, the frequency dependence of the array formation process permits the experimental determination of the characteristic frequency, $\omega_R$. For a homogeneous population of particles, the determination of the relaxation frequency is determined by inducing a transition in the array configuration particle arrays assembled under the condition $\omega < \omega_R$ assume a closepacked configuration; when the frequency is then tuned to $\omega > \omega_R$, arrays undergo a transition to an expanded configuration [Chau et al, Proc. SPIE, 3877, 36–42]. Accordingly, the frequency of the applied AC electric field is first set to a sufficiently low value so as to enable the assembly of an array within a designated area and is then set to progressively higher values to trigger the transition to an expanded array configuration.

For a heterogeneous mixture of particles disposed on a patterned electrode surface, the entire set of relaxation frequencies characterizing the types of given particles maybe determined as follows. The frequency of the applied AC electric field is first set to a sufficiently high value so as to prevent transport of any particles into designated areas of low impedance, and is then set to progressively lower values to permit array assembly for those particles satisfying the criterion $\omega \leq \omega_R$.

Particle Size—Using this transition in array configuration to determine $\omega_R$, the relation between $\omega_R$ and particle size may be determined for different electrolyte concentrations and for particles displaying different surface properties (see Example 2).

Surface-Chemical Composition—For given size, $\omega_R$ also varies with particle surface chemistry. For example, when proteins are coupled to bead surfaces, $\omega_R$ decreases; when oligonucleotides are coupled to protein-coated beads, $\omega_R$, increases. In general, both the local density of charge carriers, n, as well as their ionic mobility, u, may be affected.

Non-aqueous Electrolytes—Rectified field-induced fluid flow as well as particle transport and array assembly, the latter accompanied by an acceleration across impedance steps, also occur in non-aqueous suspensions. The relaxation frequency of particles assembled in DMSO and acetonitrile is shifted to lower values when compared to aqueous suspensions.

IV. Fractionation of Heterogeneous Particle Mixtures

The characteristic dependence of $\omega_R$ on particle size and surface chemical composition, manifesting itself in its effect on particle transport and array assembly under conditions characteristic of LEAPS as described herein, provides the basis for an on substrate (e.g., on-chip) method to fractionate complex heterogeneous mixtures of particles including suspensions of cells. The underlying principle of operation of the method of the present invention is to form designated areas of low impedance of an EIS interface, either by interfacial patterning or by illumination as provided in LEAPS, and to select a frequency, or sequentially select multiple frequencies, of the applied voltage, under conditions compatible with the aggregation of at least one constituent subset among a given, heterogeneous set of particles.

The fractionate a mixture composed of two different types of beads that differ in their respective relaxation frequencies, the frequency of the applied voltage is set to an intermediate value to selectively assemble arrays of beads of the higher relaxation frequency. In accordance with the dependence of relaxation frequency on particle size, as disclosed herein, the condition $\omega_R^L < \omega < \omega_R^S$ ensures that only the smaller particles (characterized by a frequency $\omega_R^S$) enter the region of lower impedance, while larger particles (characterized by a frequency $\omega_R^L$) align on the high impedance side of the feature (see Example 4). Similarly, the dependence of the relaxation frequency on surface chemical composition can be used to fractionate particles (see Example 5).

Figure 8:
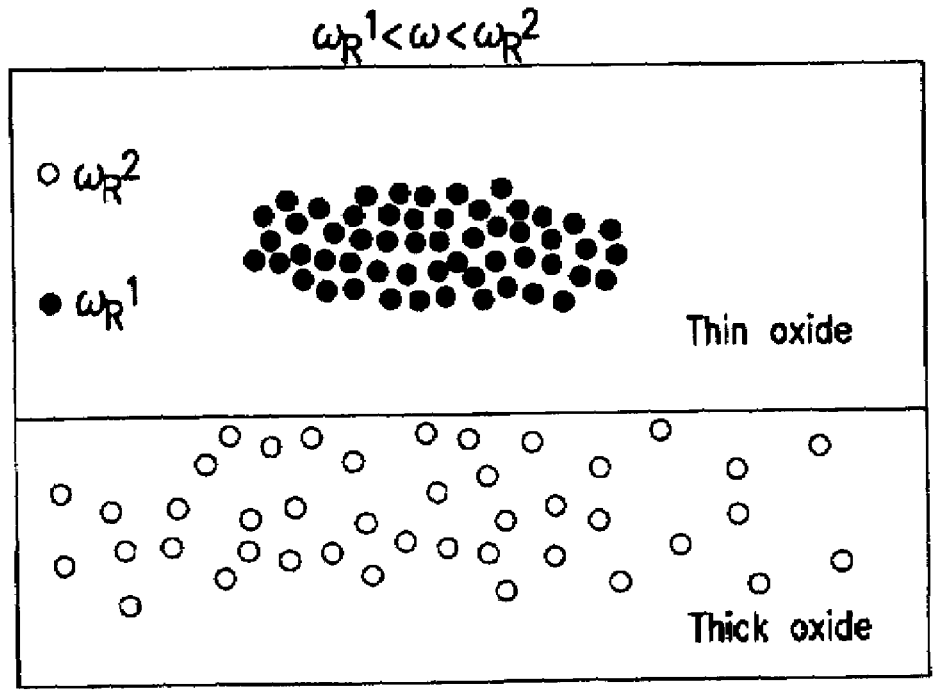
FIG. 8 is an illustration of the process particle fractionation by selection of frequency, $\omega(\omega_R^1 < \omega < \omega_R^2)$ from an initially random binary mixture of particles having two different relaxation frequencies ($\omega_R^1$ and $\omega_R^2$, $\omega_R^1 > \omega_R^2$) using a substrate surface featuring a half plane of lower impedance adjacent to one of higher impedance.

The binding of ligands to the surface of functionalized beads that produce a change in surface chemical composition can be detected on the basis of the corresponding shift in relaxation frequency. In its simplest format, the process is illustrated by the selective aggregation in a low impedance area of the electrode of only one of an originally randomly mixed set of two types of particles, with respective relaxation frequencies $\omega_R^1 < \omega_R^2$, by selection of the operating frequency, $\omega_R^1 < \omega_R < \omega_R^2$, as illustrated in FIG. 8.

This fractionation process of the present invention may be generalized to multi-component mixtures by progressively selecting frequencies to isolate and assemble one constituent subset of beads. The method of the present invention also applies to cells whose differential adhesion properties provide an additional discriminating feature for LEAPS-mediated fractionation. By the method of the present invention, different types of bead and cells are fractionated and sorted without the need for complex and expensive equipment such as flow cytometers.

As with the method disclosed herein, polarization-dependent forces also play a role in dielectrophoretic methods for fractionation of heterogeneous cell populations. However, the methods of present invention provide several distinct advantages, including:

the combination of electrokinetic flow and polarization-dependent particle responses in a collective process of particle array assembly, thereby providing for the integration of particle transport with fractionation in designated areas of an electrode;

fractionation on the basis of surface chemical properties, thereby providing for the detection of changes in the surface composition of particles or cells in the course of binding assays;

sequential multi-step fractionation within substantially the same area of a substrate under optical monitoring;

fractionation by multiple parameters including size, surface composition and selective adhesion;

multi-dimensional fractionation, e.g., frequency dispersion of array assembly, followed by selective adhesion;

parallel, multi-contrast mode of detection via optical imaging;

ease of use due to simple handling of electric contacts and; flexible electrode patterning by standard methods of semiconductor processing;

compatibility with dielectrophoretic separation processes;

optical programmability as provided by Seul and Chau [Chau et al, Proc. SPIE, 3877, 36–42].

Several related distinctions may be drawn between the method of the present invention and dielectrophoretic methods of particle separation including:

Underlying Process—The concentration polarization process invoked by the present invention, detectable by dielectric spectroscopy of particle suspensions [Minor et al, J. Colloid & Interface Science 206, 397–406 (1998)], probes molecular configurations and transport phenomena associated with particle surfaces. For particles within the range of sizes of typical interest to the applications considered herein (0.1 μm–10 μm), this process is associated with characteristic relaxation frequencies in the range of a few hundred Hz to a few tens of kHz, a range comprising AC field-driven electrokinetic flow phenomena associated with the electrode surface [Yeh et al, Nature 386, 57–59 (1997)].

In contrast, representative implementations of dielectrophoretic methods for fractionation of particle mixtures developed by Pethig's group [G. H. Markx, M. S. Talary, R. Pethig, J. Biotechn 32, 29–37 (1994)] and by Gascoyne's group [Y. Huang, X-B. Wang, F. F. Becker & P. R. C. Gascoyne, Biophys. J. 73, 1118–1129 (1997)] use the frequency-dependent transition from a positive to a negative dielectrophoretic response of cells at high frequency (typically exceeding 100 kHz) to distinguish between cell types; this transition, detectable by the response of individual cells to rotating electric fields in electrorotation measurements, reflects the relative contributions of the dielectric permittivity and membrane conductance to the overall dielectric response of cells [Jones, "The Electromechanics of particles", Cambridge University Press, Cambridge, UK 1995]. In contrast to the collection of particles over macroscopic distances afforded by electric-field-induced fluid flow in accordance with the present invention, the prior art relating to dielectrophoretic methods of particle fractionation does not invoke electric field-induced fluid flow in the fractionation process.

Electric Field Configuration—As with LEAPS, the configuration of electric fields according to the method of the present invention is produced by applying an AC voltage normal to the EIS interface, for example by adopting a sandwich configuration in which the voltage is applied between a pair of parallel planar electrodes confining the electrolyte solution. That is, the applied field is nominally normal to the electrode surfaces. In contrast to the methods of the present invention, voltages in these dielectrophoretic methods of separation are not applied across the fluid gap, but are instead applied between pairs of electrodes deposited on the same surface. Because the forces of interest in these methods of the prior art are of very short range, arising primarily from the spatial inhomogeneities of the "fringe" fields at the electrode edges, designs typically employ sets of closely spaced metal electrodes of opposite polarities.

Pethig and colleagues use interdigitated, "castellated" microelectrode designs and scan frequency to separate cells by positive and negative dielectrophoresis; for example, a range of frequency can often be found in which viable cells experience positive dielectrophoresis while non-viable cells experience negative dielectrophoresis. Differential forces of retention strongly confine cells under positive dielectrophoresis, permitting cells experiencing negative dielectrophoresis to be swept away by an externally provided lateral fluid flow. Gascoyne and colleagues have devices a dielectrophoretic levitation method in which traveling wave dielectrophoresis is combined with externally driven laminar flow along the electrode surface in a field-flow fractionation process in which the differential dielectrophoretic lift of different types of cells exposes them to different flow velocities of a parabolic flow profile maintained in the separation chamber. Entrained by the flow, cells are detected, one at a time, as they traverse a downstream cell counter.

Simultaneous Transport and Assembly—The LEAPS-enabled fractionation method of the present invention combines electrokinetic flows with concentration polarization in a collective process to integrate flow-mediated particle transport with the differential response to ponderomotive forces to bring about both the long-range transport of particles ("collection") as well as fractionation in the process of array assembly. The frequency ranges typically employed in dielectrophoretic analysis exceed the characteristic relaxation frequencies associated with electric field-induced electrokinetic flows, a fact which has profound consequences for the design of electrode configurations permitting the short-ranged dielectrophoretic forces to be utilized for particle collection. Voltage switching strategies (as for example in traveling wave dielectrophoresis), enabling serial transport and fractionation of particles, however, suffer from the disadvantage that it requires complicated electrode configurations and design.

Optical Programmability—The method of the present invention is unique in providing for real-time control of fractionation processes by means of light-induced interfacial impedance modulations afforded by the programmable generation of illumination patterns.

V. Particle Analysis

The present invention includes a method of analyzing particles based on the analysis of particle transport in the course of particle array assembly in accordance with LEAPS. To that end, the equation of motion of a spherical particle including viscous drag and ponderomotive forces may be written in the form:

$$\frac{4}{3}\pi a^3 \rho \frac{dv_b}{dt} = -6\pi\mu a(v_b - v_f) + K(\omega)\nabla E^2 \qquad (9)$$

where $v_b$ and $v_f$ respectively denote the velocity of the particle and the fluid medium and $K(\omega)=2\pi a^3 \epsilon_M k$, where k is defined in connection with Eqs (1) and (2). The ponderomotive force will vanish as $k \to 0$ or $\epsilon_S \to \epsilon_M$. Reference to FIG. 2 shows that this condition corresponds to relaxation: as the frequency of the external electric field approaches $\omega_R$, the fully polarizable state is no longer attainable. In general, $v_{max}$ will thus depend on surface potential, ion mobility and frequency.

This equation may be used to analyze the motion of particles in the course of particle collection and array assembly by implementing the following steps:

1. For a given EIS patterning geometry, specified, for example, in the form of the electrode surface potential, $\phi_S(x, y)=\phi(x, y, z=0)$, solve the Laplace equation to obtain the potential and the electric field distribution, $E(x, y, z)=-\nabla\phi(x, y, z)$; for several relevant configurations, analytical models of $\phi_S(x, y)=\phi(x, y, z=0)$ are available (see Example 1);

2. Evaluate the term $\nabla(E \cdot E)$;

3. Evaluate the electrokinetic fluid velocity, of $v_f^{max}=\epsilon/\mu \nabla\phi$, at the slipping plane of the electrode; this serves as the boundary condition for the evaluation of the flow field above the electrode, further assuming the fluid to be static at infinite distance from the electrode;

4. Determine $K(\omega)$ using the expression; $K(\omega)=2\pi a^3 \epsilon_M (\epsilon_s(\omega)-\epsilon_M)/(\epsilon_s(\omega)+2\epsilon_M)$;

5. Determine the particle velocity, $dx_b/dt=v_b(t)+v_f(t)$, in the particle moving frame; the maximum (relative) particle velocity, $v_{max}$, is attained in the vicinity of steep impedance gradients; determine the particle position, $x_b=x_b(t)$;

6. Determine (using the functions obtained in steps 4 and 5), the particle velocity as a function of position; $dx_b/dt=f(x_b)$.

Figure 5:
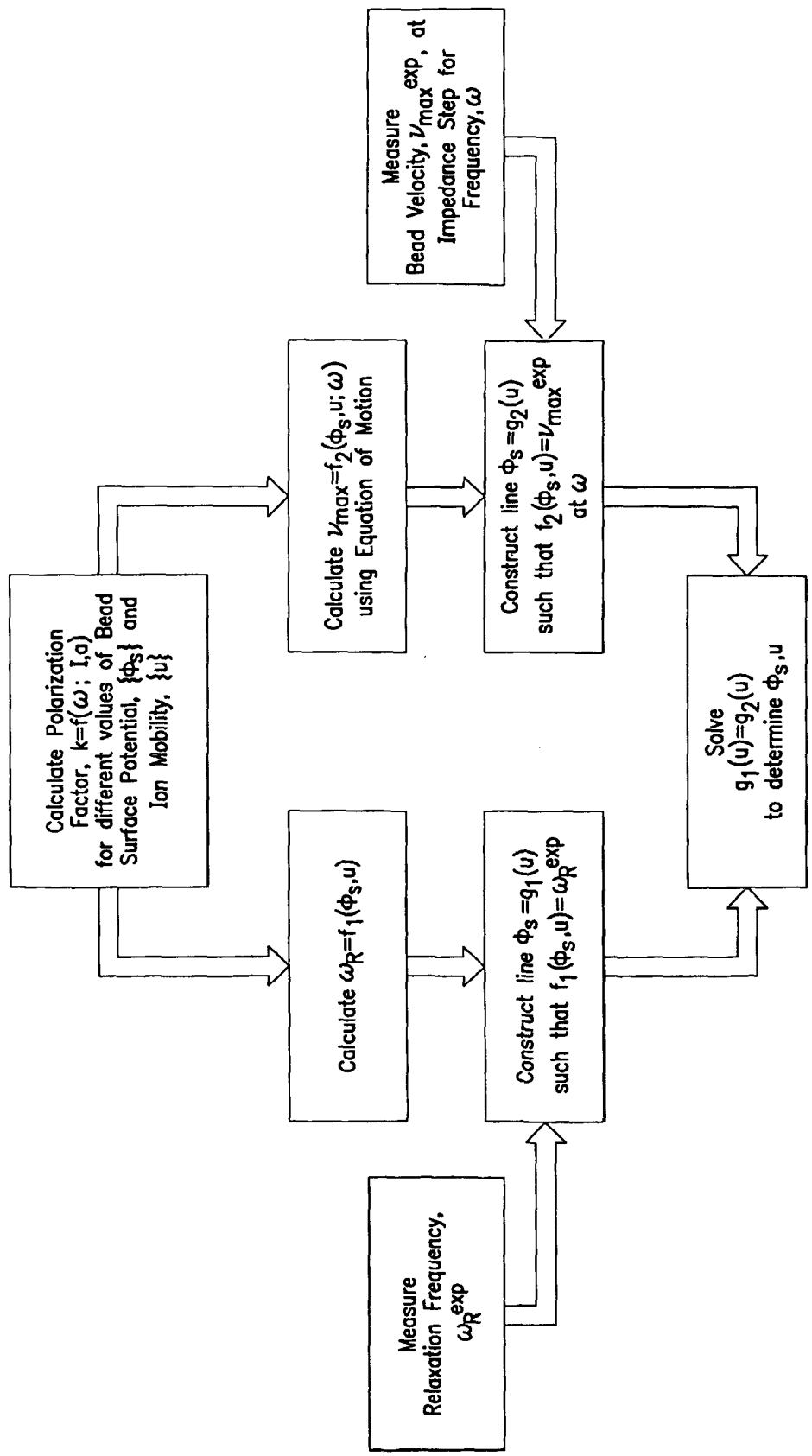
FIG. 5 is a flow chart summarizing an analytical procedure for the simultaneous determination of particle surface potential and surface conductance from experimentally determined values of particle velocity during array assembly and particle relaxation frequency. Also indicated are the computer programs ("Codes") generated to perform the calculations.

In certain embodiments of the present invention, the algorithm detailed in the flow chart presented in FIG. 5 is used to convert the experimentally determined values for the relaxation frequency, $\omega_R$, and the frequency-dependent maximum particle velocity, $v_{max}$, attained near impedance gradients (see e.g. FIG. 6) into the particles' surface ("zeta") potential, $\phi_s$, and surface conductivity, $\sigma$. As indicated in FIGS. 3 and 7, both $\omega_R$ and $v_{max}$ depend on surface potential and ionic mobility and the determination of a pair of parameters ($\phi_s$, u) such that $\omega_R=\omega_R^{exp}$ and $v_{max}=v_{max}^{exp}$ is carried out using numerical analysis as summarized in the flow chart. The present invention also includes a method for particle analysis that allows simultaneously determination of morpholgical parameters such as size and shape along with the electrical parameters in a miniaturized imaging format.

This method provides the basis for a quality control technology that is particularly sensitive to surface functionalization. In addition, the method provides the basis to detect the binding of biomolecules to "matching" molecules displayed on the bead surface. That is, the change in surface chemical composition that results from the binding of certain molecules to particle or cell surfaces is detected without the need for fluorescent or other optical labeling.

The present invention will be better understood from the Experimental Details that follow. However, one skilled in the art will readily appreciate that the specific methods and results discussed are merely illustrative of the invention as described in the claims which follow thereafter.

EXAMPLES

General Experimental Conditions:

Preferred particle array assembly is carried out in fluidic microcells which are formed by sandwiching a double-sided Kapton spacer of ~100 µm thickness between a 1 cm×1 cm substrate that can be patterned electrically, such as a silicon chip (n-type, capped either by a uniform or a lithographically patterned thin $SiO_2$ layer), also serving as the bottom electrode, and a glass cover slip coated with indium tin oxide (ITO) to a typical sheet resistance of 1400 Ohm Square serving as the top electrode. AC voltages of 1–10 $V_{p-p}$, in a frequency range from 100's of hertz to a few kilohertz are applied between the electrodes across the fluid gap. Particle transport and assembly were monitored by video microscopy permitting frame capture and digitization of frames for further analysis.

Aqueous Suspensions—Prior to assembly, particles stored in buffer are washed and resuspended in deionized and ultrafiltered water (conductivity <50 S cm$^{-1}$); in some cases, salt ($\leqq$1 mM) is added to provide buffering. Anionic and cationic particles from 0.5 µm to 10 µm in diameter, composed of silica or modified polystyrene and functionalized with a variety of chemical surface groups, as well as functionalized core-shell particles obtained from a variety of manufacturers have been used. These particles were further modified to display oligonucleotides, DNA fragments or proteins.

Non-Aqueous Suspensions—Illustrative of these systems are: DMSO($\epsilon_{DMSO}$=47.24): 4.4 µm carboxylated PS particles (Dyno, Oslo, Norway); 2.1 µm carboxylated PS particles stained with fluorescein (Molecular Probes, Eugene, Oreg.); in both these cases, stock particles originally suspended in water/buffer, were resuspended in DMSO by way of several successive cycles of centrifugation and resuspension to exclude water. Glass beads (3–10 µm in diameter) (Polyscience, Pa.); stock particles, supplied in dry powder form, were resuspended in the solvent of choice prior to assembly. Acetonitrile ($\epsilon_{acetonitrile}$ 36.64): 1 µm nonporous oxirane acrylate beads (Sigma, Mo.); procedure analogous as in the case of glass beads.

Example 1

Particle Array Assembly: Half-space Geometry

Figure 6:
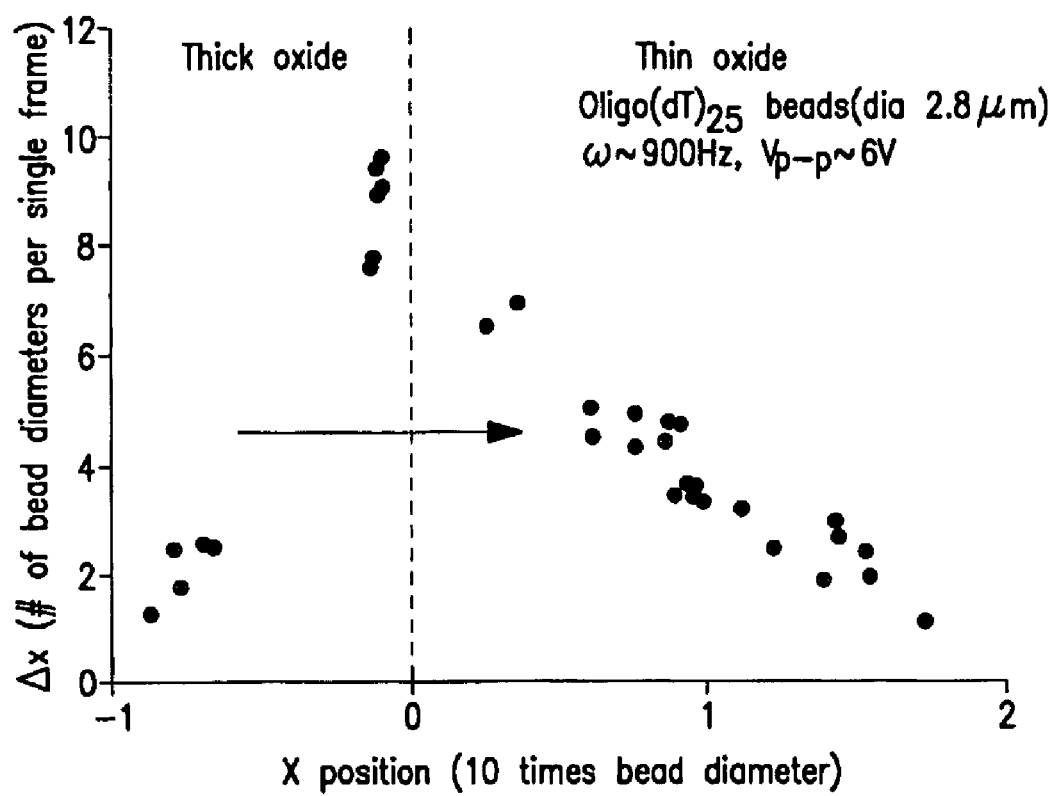
FIG. 6 is an illustration of particle movement and of the relative position of each particle relative to a position defined as x=0. The result of such particle movement is array assembly and each particular particle position represents a stage in the assembly process. The particles assemble in thin oxide region of the silicon/silicon substrate and the demarcation between thin oxide and thick oxide defines the position x=0.
Figure 7A:
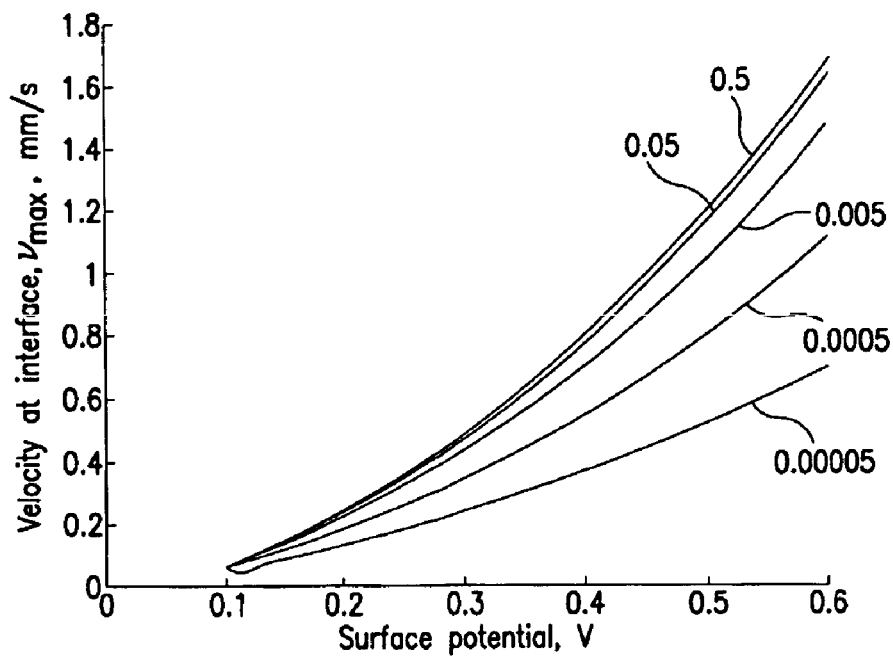
FIG. 7(A) is an illustration of the particle velocity at the interface as a function of surface potential, as evaluated numerically on the basis of the theoretical model described herein in for several ratios of the counterion mobility to the bulk ion mobility, as indicated in the legend. (B) is a plot of the relation between surface potential and mobility for the specific bead velocity of 0.8 mm/s.
Figure 7B:
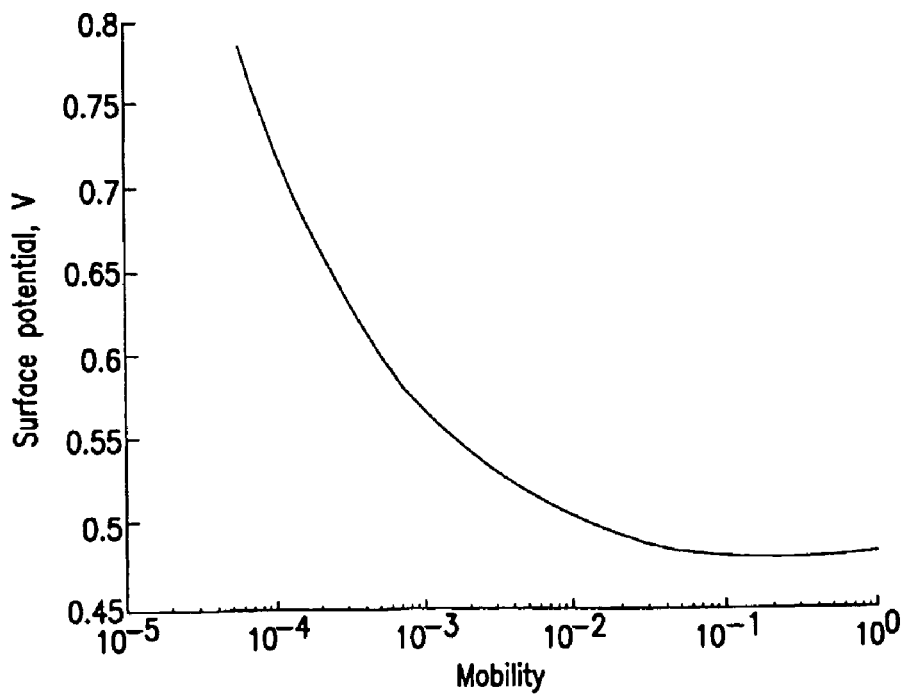

FIG. 6 displays bead velocities measured in the course of array assembly of oligo-dT(25) particles of diameter 2.8 µm (obtained from Dynal, Oslo, Norway) using κα≅45 (see also the conditions shown in the inset of the lower panel) and invoking video microscopy. Analysis of the "streaking" in the snapshots in the upper portion of FIG. 6, taken with 1/30 s exposure, reveals the significant acceleration of particles traversing the impedance step, created by a variation in oxide thickness from ~1000 Å to ~100 Å. Visual inspection also reveals that particles are simultaneously displaced toward the substrate. The instantaneous velocities extracted by image analysis of a series of snapshots are plotted in the lower panel of FIG. 6. Arrays of assembled particles act in the manner of low impedance regions of the substrate: they generate in-flow directed toward the array perimeter and attract additional particles which accelerate toward the array.

The numerical solution of the equation of motion, given an impedance step in a "half-space" geometry, reveals a strong dependence of $v_{max}$ on surface potential for several ratios of $u/u_\infty$ and for given particle size, as illustrated in FIG. 7. This is as expected: a high surface potential corresponds to a large induced dipole moment and hence to a large ponderomotive force; in contrast; the dependence on ion mobility is weak.

The equation of motion takes into account the ponderomotive forces, the drag forces and also the moving frame of reference of the fluid. The path of any bead can be simulated given the experimental conditions such as voltage, gap size, ionic strength, ion mobilities, oxide thicknesses and given pertinent bead properties such as size and surface potential. In general, it is desirable to apply the numerical model to fit experimental data and so to improve the accuracy of the determination of $v_{max}$.

Figure 9:
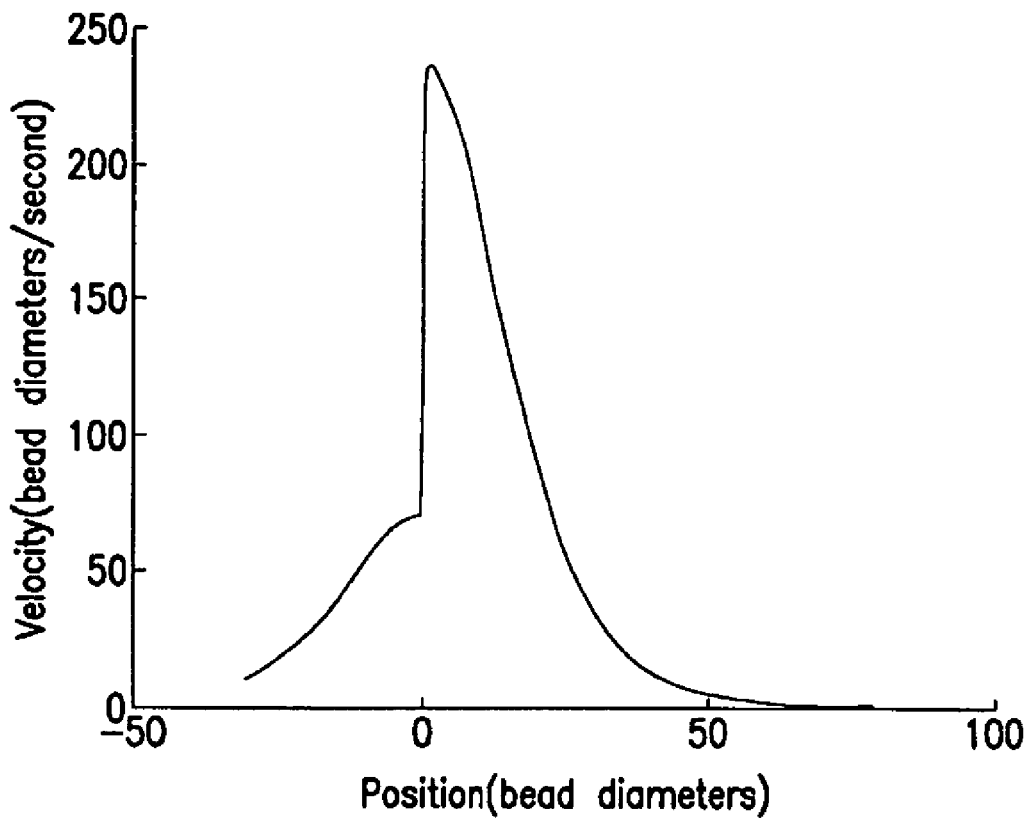
FIG. 9 is an illustration of the determination of the velocity of particles experiencing acceleration as they cross a boundary, located at position "0", separating regions of high and low electrode impedance.

A typical solution of the equation of motion, generated numerically by representing the "half-space" geometry by a surface potential profile in the form $\phi_s$=A tanh(κx), is shown in FIG. 9. The origin of the graph represents the location of the impedance step. The position of the bead is negative when it is in the thick oxide region, where the velocity of the bead is determined by the fluid velocity at any given point. However, when approaching the impedance step to within a distance of the order of the Debye length, the bead experiences the aforementioned ponderomotive force which causes it to accelerate across the step relative to the fluid. Given the short range of ponderomotive forces (~$\nabla E^2$), the acceleration ceases within a short distance of the step, and the bead experiences a drag force which decelerates it to the velocity of the surrounding fluid. At larger distances from the step, the lateral fluid motion ceases and consequently, the bead comes to rest unless the ponderomotive forces surrounding pre-existing bead arrays or clusters provide an additional acceleration toward the array boundary.

Example 2

Figure 10:
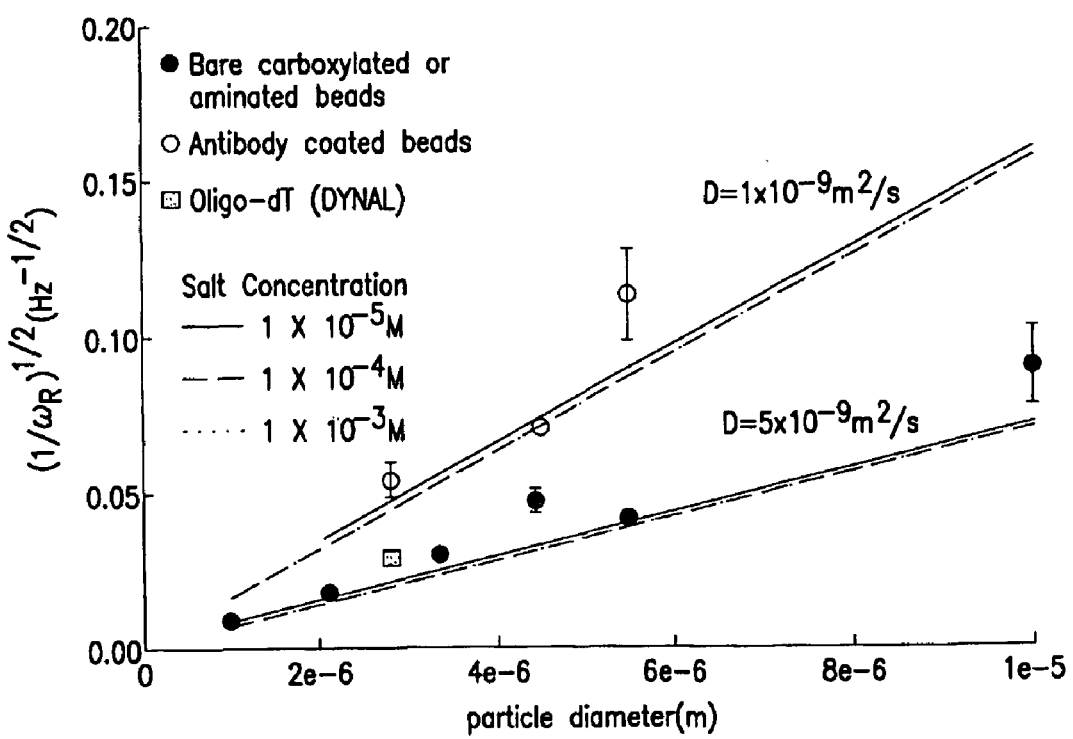
FIG. 10 is an illustration of experimentally determined dependence of particle relaxation frequency on particle diameter for three different types of particles. Experimental details are indicated in the inset to the graphical display. The results for three different salt concentrations are shown for two ionic diffusion coefficients. Results show that the relaxation frequency is not significantly affected by a change in salt concentration.

Dependence of Relaxation Frequency, $\omega_R$, on Particle Size and Composition FIG. 10 displays the results of determining the relaxation frequency by inducing an array expansion for a variety of particle sizes and for different types of particle surface chemistries. In a first group, particles included were carboxylate-modified or amine-modified polystryrene particles (obtained from Dyno, Oslo, NO) as well as "oligo-dT(25)" particles (obtained from Dynal, Oslo, NO). In a second group, particles were coated with a monoclonal antibody against interleukin-6 (obtained from R&D Systems, Minneapolis, Minn.). The anticipated scaling behavior of the relaxation frequency, $\omega_{R^{1/2}}$~α (particle size), as discussed herein, is confirmed by the experiments.

The solid lines represent a fit of the data to a simple expression discussed herein and produces a diffusivity parameter, D, which reflects the local ion-mediated surface conductance, as discussed herein. Invoking Eq. 4, the data in FIG. 10 may be interpreted to indicate that, for given $\alpha$ and $\kappa$, the binding of proteins, or other large molecules to the bead surface reduces the surface conductivity, $\sigma \sim e^2 n/f$, introduced herein.

Example 3

Particle Analysis

From experiments illustrated in FIGS. 6 and 10, values for the maximum velocity of beads traversing the step from thick oxide to thin oxide, $v_{max} \simeq 0.8$ mm/s, and the relaxation frequency, $\omega_R \simeq 2$ kHz, were determined. The theoretical model and algorithm underlying FIGS. 3, 5 and 7, yield corresponding values of $\phi$, $\simeq 0.5$V and $u/u_\infty \simeq 3.9 \times 10^{-3}$; this combination in turn yields a value of a $\sigma \simeq 0.15$ S/m and Du$\simeq$290; here, $u_\infty \simeq 0.02$ Sm$^2$/C, as determined from the tabulated molar conductivity for Na$^+$. The value for $\phi_s$ may be compared to the surface potential of ~330 mV corresponding to the titratable charge of carboxylate-modified polystyrene particles of 1 COO$^-$/4 Å$^2$ or 400 µC/cm$^2$; the results obtained indicate that the effective surface charge of oligonucleotide-modified particles substantially exceeds that of carboxylate-modified particles. The value for $\omega_R$ indicates the surface mobility of small cations relevant to the experiments to be smaller by a factor of $\geq 100$ than the mobility in the bulk; however, the surface conductivity still exceeds the bulk conductivity by two orders of magnitude, reflecting the high value of the surface potential.

Example 4

Fractionation of Particle Mixture Using Size-Dependence of $\omega_R$

Figure 11:
FIG. 11 is an illustration of the process of fractionation of an initially random particle mixture composed of larger and smaller particles on the basis of particle size using a substrate surface featuring a strip of lower impedance (bright area) surrounded by areas of larger impedance (dark areas).

FIG. 11 illustrates the fractionation of a binary mixture of smaller (2.1 µm diameter, characteristic frequency $\omega_R^S$) and larger (4.5 µm diameter, characteristic frequency $\omega_R^L$) particles using a surface design in which a region of lower interfacial impedance is created by a variation in oxide thickness from ~1000 Å to ~100 Å within the stripe indicated by lighter shading (see also Example 1). When the frequency, $\omega$, of the applied voltage adjusted such that $\omega_R^L < \omega < \omega_R^S$, only the smaller particles experience an acceleration toward the lower impedance region where they assemble into an array. By narrowing or widening the stripe, flow along the stripe also may be generated and may serve as the basis for two-dimensional fractionation in the cross-flow so realized.

Example 5

Fractionation of Particle Mixture Using Composition-Dependence of $\omega_R$

Figure 12:
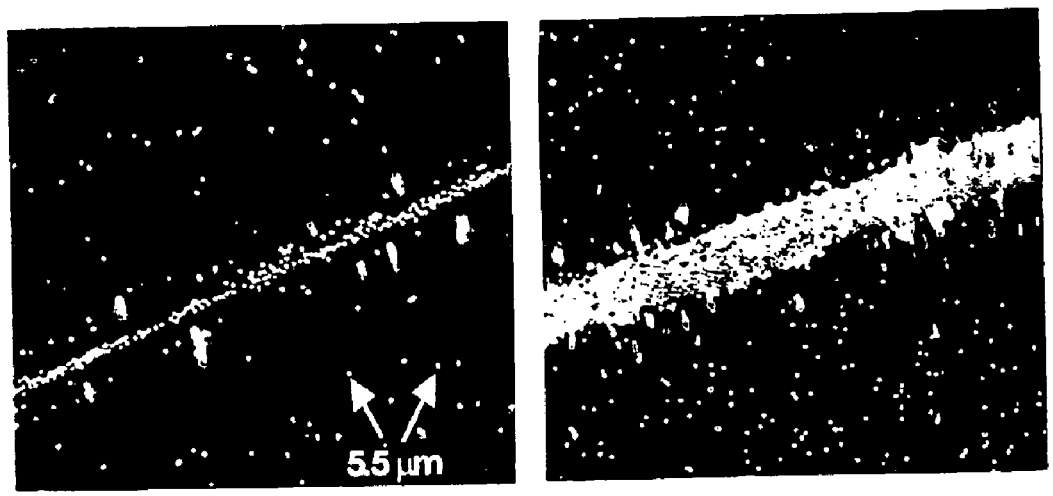
FIG. 12 is an illustration of the two successive stages in the process of fractionation of an initially random particle mixture composed of particles of identical size.

FIG. 12 illustrates the fractionation of a binary mixture of red and blue particles of identical size but differing surface chemical composition. The relaxation frequency, $\omega_R^{bare}$, of carboxylate-modified particles, tagged with a green dye, is lowered by binding of protein, tagged with a red dye, to a characteristic frequency, $\omega_R^{mod}$. Under the condition $\omega_R^{mod} < \omega < \omega_R^{bare}$, only the unmodified particles enter the stripe region of lower impedance, while modified, protein-coated particles align on the high impedance sides of the feature. The magnitude of the shift in characteristic frequency is determined by the amount of bound protein.

Example 6

Detection of Protein Binding to Beads or Cells without the Use of Tags

A molecular binding event on a known particle surface causing a change in the surface chemical property (i.e. a change in the dielectric property of the particle plus bound molecule over that of the particle) can be easily be detected utilizing the fact that the effect of the binding is reflected in change in the relaxation frequency of the particle. For example, FIG. 10 illustrates the experimentally evaluated change in relaxation frequency of a particle which display, on its surface, either carboxylate groups or carboxylate plus captured layer of antibody. The binding of antibody to the particle surface lowered the characteristic frequency, $\omega_{mod}$, of modified particles relative to the characteristic frequency, $\omega_{bare}$, of unmodified particles. Similarly, the binding of biotinylated oligonucleotide probes on the surface of a streptavidin functionalized particle may be detected. The binding of the oligonucleotide fragment increased the characteristic frequency, $\omega_{mod}$ of oligo bound particles relative to the characteristic frequency, $\omega_{bare}$, of unbound particles.

Example 7

Frequency-Dependent Collection and Assembly of Human Myeloid Cells

Figure 13:
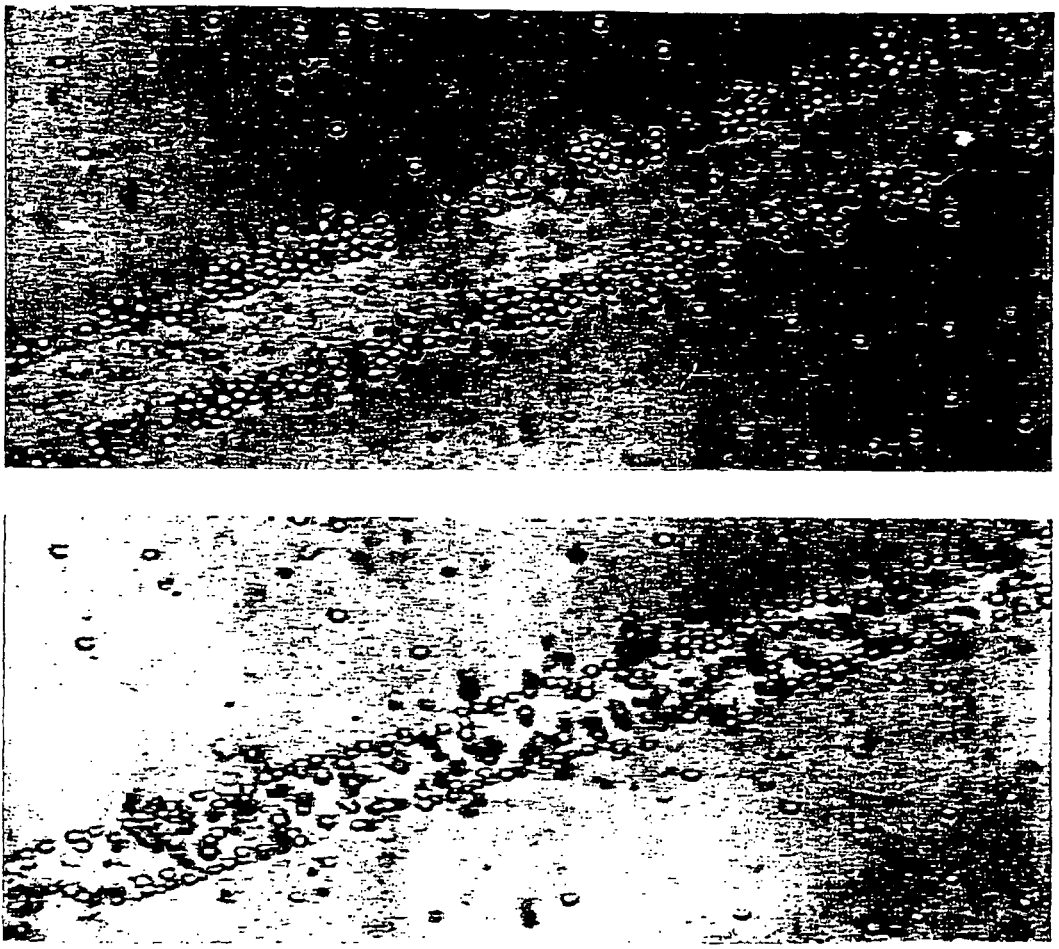
FIG. 13 is an illustration of the collection and assembly of HL-60 Human Myeloid Cells (~15 μm diameter) in characteristic configurations on a patterned silicon chip.

FIG. 13 illustrates the collection and enrichment of HL-60 human myeloid cells (CCL-240, obtained from ATCC and maintained for experiments in 8.5% sucrose/0.3% dextrose) in designed areas of a patterned silicon substrate. Using silicon chips with patterned oxide surfaces featuring a stripe of thin oxide ($\leq 100$ Å) typically 100–200 µm in width delimited by "steps" in impedance indicated by the change in brightness, application of a voltage of 5V peak-to-peak, with frequency set to the values indicated in the two panels in the figure, produces aggregates of either adjacent to, or within the designated stripe, reflecting the selection of the frequency in the applied voltage.

Example 8

Assembly of Bacterial Cells and Fractionation by Selective Adhesion

Figure 14:
FIG. 14 is an illustration of the collection and assembly of E. coli and staph bacterial cells (~1 μm diameter) in characteristic bands on a patterned silicon chip.

FIG. 14 illustrates the collection and enrichment of *E. coli* and *Staphylococcus epidermis* bacterial cells, serving as respective model systems for Gram-negative and Gram-positive bacteria, in different regions of a patterned substrate (here a silicon chip). That is, using chips with patterned oxide surfaces featuring a strip of thin oxide ($\leq 100$ Å) typically 100–200 µm in width, application of a voltage of 5 V peak-to-peak across a fluid gap of 100 µm and frequency set to 2 kHz produces "bands" of cells in positions reflecting the preferential adhesion of *S. epidermis* near the "step" in impedance indicated by the change in brightness and *E. coli* in the center of the strip. The position of the bands is thus characteristic of bacterial type.

Example 9

Strength of Adhesion

Cell rolling along a surface is the initial step in many kinds of inflammatory response. The present invention provides for the experimental determination of the strength of adhesion between cells of interest or ligand-functionalized microparticles disposed on a receptor-functionalized electrode surface. For example, given a patterned electrode surface as described, low-impedance regions can coated with E-Selectin to investigate the assembly of HL-60 cells (see example 7). Under the action of LEAPS-mediated flow, cells, while being transported toward low-impedance regions of the electrode surface, exhibit rolling and sticking, the latter representing a manifestation of a positive adhesive interaction between cells and surface. In-vitro assays have been described which use the rolling of cells or ligand-functionalized microparticles on a receptor-functionalized surface that is exposed to tangential fluid flow to estimate the strength of adhesion between cells or microparticles and the surface [Brunk, D. K., and Hammer, D. A., Biophysical Journal, 72, 1997, 2820–2833; Hammer, D. A., and Apte, S. M, Biophysical Journal, 63, 1992, 35–57; Springer, T., Cell, 76, 301, 1994.]. The analysis of rolling and sticking of HL-60 cells on E-Selectin coated glass wafers under the presence of pressure driven flow has been used for anti-inflammatory drug screening [Mossavi et al., Proceedings of MicroTAS '98 Workshop, D. J. Harrison and A. van den Berg (Eds.), 69–72, 1998]. The present invention provides a superior mode of flow control by way of LEAPS. For example, a receptor-functionalized electrode on which cells or microparticles of interest have been disposed in predesignated areas can be exposed to LEAPS-mediated fluid flow (see FIG. 4) whose direction and strength are readily controlled. This permits the evaluation of the correlation between the strength of the flow-induced shear stress acting on the adsorbed cells or particles and the efficiency of the hydrodynamic detachment, which in turn permits an estimation of the adhesive forces operative between the cell or particle and said surface.

Example 10

Multi-dimensional Fractionation

In multi-dimensional fractionation, a mixture of particles is separated into subpopulations in two or more stages in accordance with multiple discriminating parameters. Here, in addition to the frequency dispersion of field-induced polarization other attributes such as differential selective adhesion etc. can be used. For example, a mixture of HL-60, *E. coli* and *S. epidermis* can be fractionated using patterned chips featuring a strip of thin oxide ($\leq 100$ Å) typically 100–200 µm in width. Application of a voltage of 5 V peak-to-peak across a fluid gap of 100 µm and frequency set to 2 kHz produces "bands" of cells in positions reflecting the preferential adhesion of *S. epidermis* near the "step" in impedance and *E. coli* in the center of the strip. Under this condition the HL-60 cells form linear chains at the thick-thin oxide boundary which extend to the thick oxide region (see example 7).

Example 11

Sequential Light-directed Fractionation of Multi-component Mixtures

Figure 15:
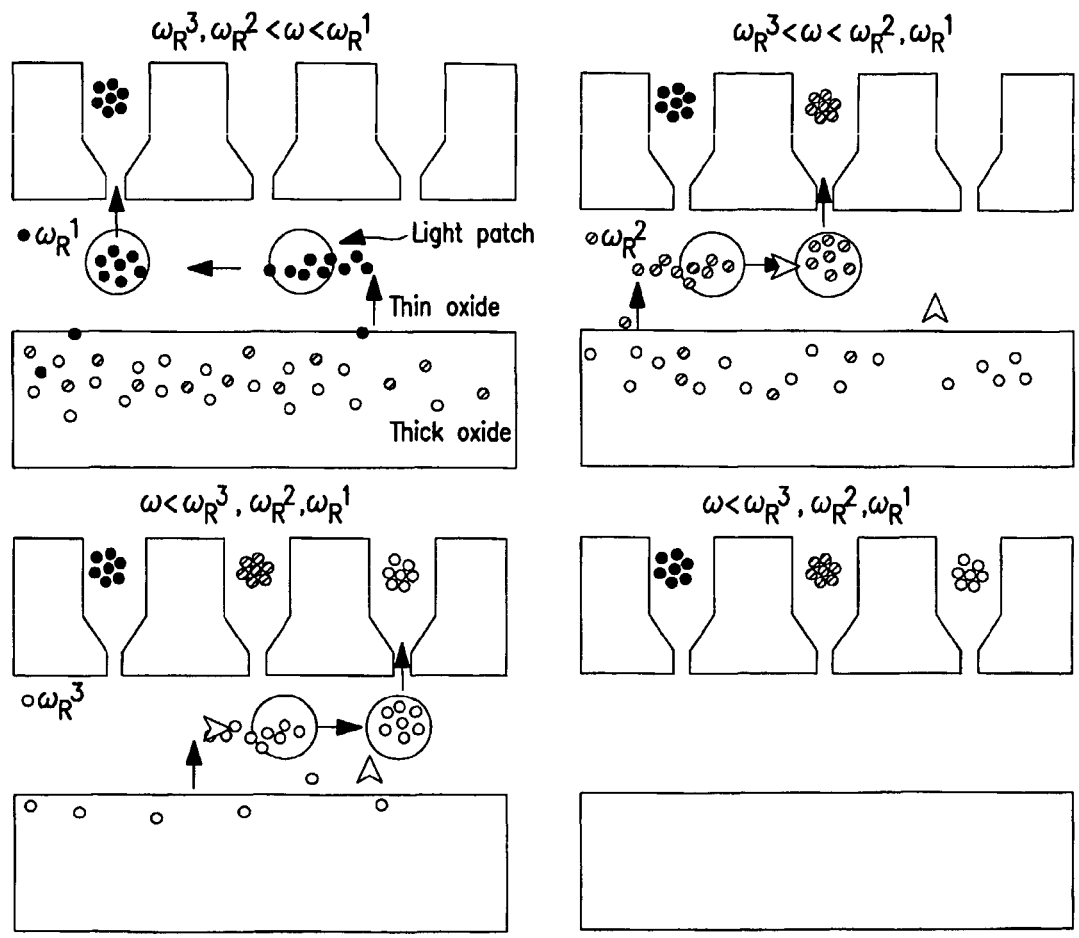
FIG. 15 is an illustration of serial fractionation of a multi-component particle mixture (with each particle type possessing a unique relaxation frequency ($\omega_R^i$)) using patterned electrode and sequence of illumination patterns.

A multi-component particle mixture in which each particle population displays a unique relaxation frequency ($\omega_R^i$) may be fractionated using a combination of a patterned electrode and illumination as illustrated in FIG. 15. Given relaxation frequencies ($\omega_R^i$) in the range $\omega_{low} < \omega_R^i < \omega_{high}$, the frequency of the applied AC electric field is scanned from the high limit ($\omega_{high}$) to the low limit ($\omega_{low}$) of the range; particles are sequentially swept into the thin oxide/low impedance collection region starting with the ones with higher relaxation frequencies. Once inside, each population is guided by light into separate thin oxide pads which are connected to the initial collection zone via narrow channels. This particular patterning will confine beads in the respective pads.

Example 12

Encoding of Particle Arrays using Engineered Particle Polarizability

Dielectric "tagging" to produce particles of desired polarizability and corresponding relaxation frequency may be used to produce a specific dependence of the particle response to LEAPS. Dielectric tagging may be accomplished by way of introducing labels to the exterior or interior of the particle. For example, metallization of particles changes their polarizability. This approach may be extended to the engineering of a particle whose polarizability is light dependent. For example, using light-sensitive tags such as $TiO_2$ nanoparticles, the polarization of a $TiO_2$-tagged particle is increased exclusively when illuminated with light [Y. Komoda, Tata N. Rao, and A. Fujishima, Photoelectrorheology of $TiO_2$ nanoparticle suspensions. Langmuir, 1997, 13, 1371–1373].

Although the invention has been described above with reference to examples and to preferred embodiments, it will be appreciated that the invention may be embodied in other forms or carried out in other ways without departing from the spirit or essential characteristics thereof. The above description is therefore to be considered in all respects illustrative and not restrictive, and all changes which come within the meaning and range of equivalency are intended to be embraced therein.

What is claimed is:

1. A method of fractionation of a mixture of particles which are suspended in an electrolyte solution between a first electrode positioned in a first plane and the surface of a second planar electrode positioned in a second plane different from the first plane, and wherein the surface or the interior of the second electrode either is or can be patterned to modify the electric field extending from the surface into the electrolyte solution, and wherein the particles comprise at least two types of particles distinguished by their respective relaxation frequencies; and generating an electric field between the first and the second electrodes by applying an AC voltage between the two electrodes, said electric field having a frequency that is less than or equal to the relaxation frequency of at least one of said particle types but greater than the relaxation frequencies of at least one other of said particle types, wherein the particles having relaxation frequencies greater than or equal to the frequency of the electric field are separated from other particles.

2. The method according to claim 1, wherein the electrode is patterned by surface oxide growth, surface chemical patterning or surface profiling.

3. The method according to claim 1, wherein the particle relaxation frequency is related to the particle size, and the particles are separated based on their respective size.

4. The method according to claim 1, wherein the particle relaxation frequency is related to the surface composition of the particles, and the particles are separated based on their respective surface composition.

5. The method according to claim 1, wherein the generation of the electric field results in formation of a planar array of substantially one layer of particles in a designated area on the second electrode surface, the particles of said planar array having the relaxation frequencies greater than or equal to the frequency of the electric field.

6. The method of claim 1, wherein the second electrode is a silicon electrode coated with a dielectric layer.

7. The method of claim 1, wherein the frequency of the electric field is from about 10 Hz to 100 kHz.

8. The method of claim 1, wherein the first electrode is optically transparent and the fractionation of the particles is monitored using a video detector or camera.

9. The method of claim 1, wherein the particle mixture comprises more than two types of particles, and the particles are fractionated one particle type at a time by adjusting the frequency to allow sequential fractionation of one type of particle at a time.

10. The method of claim 1, wherein the particles are cells.

11. The method of claim 1, wherein the second electrode is a light-sensitive electrode, and the surface is illuminated with a predetermined light pattern, said illumination in combination with the electric field and the electrode patterning resulting in separation of particles.

12. The method of claim 11, wherein the predetermined light pattern is provided by an apparatus for programmably generating and imaging onto a substrate an illumination pattern having a predetermined arrangement of light and dark zones, said apparatus comprising:
   an illumination source;
   a reconfigurable mask composed of an array of pixels, said pixels being actively controllable and directly addressable by means of a computer-controlled circuit and computer interface, said computer-controlled circuit being operated using a software program providing temporal control of the intensity of illumination emanating from each pixel so as to form the illumination pattern comprising the predetermined arrangement of light and dark zones;
   a projection system suitable for imaging the reconfigurable mask onto the substrate; and
   an imaging system incorporating a camera capable of viewing said substrate with superimposed illumination pattern.

13. A method of determining the zeta potential of particles suspended in an electrolyte solution and/or the mobility of ions or molecules within a region adjacent to said particles, the method comprising:
   suspending a plurality of particles at an interface between an electrolyte solution and a light-sensitive electrode;
   illuminating the interface with a predetermined light pattern;
   generating an electric field at the interface by application of an AC voltage, and adjusting the frequency of said electric field to produce formation of a planar array of substantially one layer of particles in a designated area on the electrode defined by the pattern of illumination;
   determining the relaxation frequency of said particles;
   determining the maximal velocity (vmax) of said particles; and
   converting the maximal velocity and the relaxation frequency to either the zeta potential or the surface conductivity of said particles, or to both the zeta potential and the surface conductivity.

14. The method of claim 13, wherein the surface potential and the surface conductivity of the particles are determined simultaneously.

15. The method of claim 14, in which the relaxation frequency of the particles is determined by measuring the highest frequency of the electric field at which the array formation takes place.

16. The method of claim 13, in which the maximal velocity is determined by measuring the velocities of the particles crossing impedance gradients in the course of array assembly.

17. The method of claim 13, in which the maximal velocity of the particles is determined by means of image analysis and particle tracking.

18. The method of claim 13, wherein the electrode is a silicon electrode which is coated with a dielectric layer.

19. The method of claim 13, further comprising an additional electrode, wherein the additional electrode and the light-sensitive electrode are substantially planar and parallel to one another and separated by a gap, with the electrolyte solution containing the particles being located in the gap, and wherein the electric field is generated by applying an AC voltage between the two electrodes.

20. The method of claim 13, wherein the method determined the mobility of ions or molecules within a region adjacent to the particles.

21. A method of determining the zeta potential of particles suspended within an electrolyte solution and/or the mobility of ions or molecules within a region adjacent to said particles, the method comprising:
   providing a first electrode positioned in the first plane and a second electrode positioned in a second plane different from the first plane, an electrolyte solution located therebetween and a plurality of particles of one or more types, each type having a characteristic relaxation frequency, said particles being suspended at an interface between the electrolyte solution and the second electrode, wherein the second electrode is a planar electrode wherein its surface or interior have been patterned to modify the electric field at the interface;
   generating an electric field between the first and the second electrode by applying an AC voltage between the two electrodes;
   adjusting the frequency of said electric field to produce particle transport into a designated area of the electrode defined by said patterning of the electrode;
   determining relaxation frequencies of said one or more types of particles;
   determining the maximal velocities (vmax) of transport of said particles; and
   determining either the zeta potential of said particles or the mobility of ions or molecules within a region adjacent to said particles, or to both the zeta potential and said mobility, based on said relaxation frequency and said maximal velocity.

22. The method of claim 21, wherein the surface potential and the surface conductivity of the particles are determined simultaneously.

23. The method of claim 21, in which the relaxation frequency of the particles is determined by measuring the frequency of the electric field at which array formation takes place.

24. The method of claim 21, further comprising the step of altering the configuration of the assembly after its formation by adjusting the frequency of the electric field, and measuring the frequency of the electric field that is associated with alteration of the array configuration.

25. The method of claim 21, in which the maximal velocity is determined by measuring the velocities of the particles crossing impedance gradients in the course of array assembly.

26. The method of claim 22, wherein the electrode is a silicon electrode which is coated with a dielectric layer.

* * * * *

UNITED STATES PATENT AND TRADEMARK OFFICE
CERTIFICATE OF CORRECTION

| | | |
|---|---|---|
| PATENT NO. | : 7,211,183 B2 | Page 1 of 1 |
| APPLICATION NO. | : 10/658070 | |
| DATED | : May 1, 2007 | |
| INVENTOR(S) | : Michael Seul, Sukanta Banerjee and Kairali Podual | |

It is certified that error appears in the above-identified patent and that said Letters Patent is hereby corrected as shown below:

Claim 20, column 24, line 36, change "determined" to --determines--

Signed and Sealed this

Second Day of September, 2008

JON W. DUDAS
*Director of the United States Patent and Trademark Office*